United States Patent [19]

Kadow et al.

[11] Patent Number: 5,773,435
[45] Date of Patent: Jun. 30, 1998

[54] PRODRUGS FOR β-LACTAMASE AND USES THEREOF

[75] Inventors: John Kadow, Wallingford; Takushi Kaneko, Guilford, both of Conn.; Peter D. Senter, Seattle; Vivekanada M. Vrudhula, Edmonds, both of Wash.

[73] Assignee: Bristol-Myers Squibb Company, Princeton, N.J.

[21] Appl. No.: 16,208

[22] Filed: Feb. 9, 1993

Related U.S. Application Data

[63] Continuation of Ser. No. 770,371, Oct. 8, 1991, abandoned, which is a continuation-in-part of Ser. No. 609,663, Nov. 6, 1990, abandoned, which is a continuation-in-part of Ser. No. 211,301, Jun. 29, 1988, Pat. No. 4,975,278, which is a continuation-in-part of Ser. No. 161,068, Feb. 26, 1988, abandoned, which is a continuation-in-part of Ser. No. 81,382, Aug. 4, 1987, abandoned.

[51] Int. Cl.$^6$ .................... A61K 47/48; C07D 501/54
[52] U.S. Cl. .................... 514/214; 540/222; 540/225; 540/226
[58] Field of Search ........................... 540/222

[56] References Cited

U.S. PATENT DOCUMENTS

| 3,355,452 | 11/1967 | Urech et al. ............................ 260/243 |
| 3,484,437 | 12/1969 | Urech et al. ............................ 260/243 |
| 4,783,443 | 11/1988 | Johnston et al. ......................... 514/19 |
| 4,975,278 | 12/1990 | Senter et al. ........................... 424/94.3 |

FOREIGN PATENT DOCUMENTS

| 1216791 | 1/1981 | Canada . |
| 142905 | 5/1985 | European Pat. Off. . |
| 0382411 | 8/1990 | European Pat. Off. . |
| 382411 | 8/1990 | European Pat. Off. . |
| 392745 | 10/1990 | European Pat. Off. . |
| 1509707 | 5/1978 | United Kingdom . |
| 88/07378 | 10/1988 | WIPO . |
| 90/07929 | 7/1990 | WIPO . |
| 91/08770 | 6/1991 | WIPO . |

OTHER PUBLICATIONS

Baldwin et al., *Lancet*, pp. 603–605, Mar. 15, 1986.
Thorpe, *Monoclonal Antibodies '84: Biological and Clinical Applications*, A. Oinchera et al., eds., pp. 475–506, 1985.
Ohkawa et al., *Cancer Immunol. Immunother.* 23:81–86, 1986.
Rowland et al., *Cancer Immunol. Immunother.* 21:183–187, 1986.
Gallego et al., *Int. J. Cancer*, 33:737–744, 1984.
Arnon et al., *Immunological Rev.*, 62:5–27, 1982.
Endo et al, *Cancer Research*, 47:1076–1080, 1987.
Moolten et al, *Immunol. Rev.*, 62:47–73, 1982.
Embleton, *Biochem. Society Transactions*, 14:393–395, 615th Meeting, Belfast, 1986.
Baldwin et al, *Monoclonal Antibodies and Cancer Therapy*, pp. 215–231, Alan R. Liss, Inc., 1985.
Lambert et al, *J. Biol. Chem.*, 260:12035–12061, 1985.
Vitetta et al, *Science*, 238:1098–1104, 1987.
Albino et al, *J. Exp. Med.*, 154:1764–1778, 1981.
Yeh et al, *J. Immunol.*, 126:1312–1317, 1981.
Parker et al, *Proc. Natl. Acad. Sci. USA*, 72:338–342, 1975.
Philpott et al, *Cancer Research*, 34:2159–2164, 1974.
Hellstrom et al, *Controlled Drug Delivery* (2d ed.), Robinson and Lee (eds.) pp. 638–639, 1987.
Stock, *Drug Design*, E.J., Ariens, ed. vol. II, pp. 532–571, Academic Press, New York, 1971.
Benn et al, *J. Chem. Soc.*, 2365–2375, 1961.
Mobashery et al, *J. Am. Chem. Soc.*, 108:1685–1686, 1986.
Mobashery et al, *J. Biol. Chem.*, 261:7879–7887, 1986.
Abraham, *Quarterly Reviews—Chemical Society*, 21:231, 1967.
Abraham et al, *Cephalosporins and Penicillins, Chemistry and Biology*, E.H. Flynn, ed., Academic Press, New York, 1972, pp. 1–26.
Myer et al, Poster from 5th International Conference on Monoclonal Antibody Immunoconjugates for Cancer (Mar. 15–17, 1990), San Diego, California.
Shepherd et al, *Bioorg. & Med. Chem. Lett.*, 1(1):21–26, 1991.
Alexander et al, *Tet. Lett.*, 32(27):3269–3272, 1991.
Mobasherry et al, *Biochemistry*, 26:5878–5884, 1987.
Albrech et al, *J. Med. Chem.*, 33:77–86, 1990.
Jones et al, *Antimicrob. Agents Chemotherap.*, 33(6):944–950, 1989.

*Primary Examiner*—Mukund J. Shah
*Assistant Examiner*—Pavanaram K. Sripada
*Attorney, Agent, or Firm*—Brian W. Poor; Thomas R. Savitsky

[57] ABSTRACT

The instant invention relates to a novel method for the delivery of antitumor drugs to tumor cells by the administration of a tumor-selective antibody-β-lactamase conjugate that binds to tumor cells, and the additional administration of a cephalosporin prodrug that is converted at the tumor site, in the presence of the antibody-β-lactamase, to an active cytotoxic drug. According to the preferred embodiment of this invention, a cephalosporin mustard has been constructed which when cleaved by β-lactamase yields a cytotoxic nitrogen mustard. The methods, antibody-enzyme conjugate, prodrugs, pharmaceutical compositions, and combinations of this invention provide for enhanced selective killing of tumor cells and are thus useful in the treatment of cancers and other tumors.

35 Claims, 12 Drawing Sheets

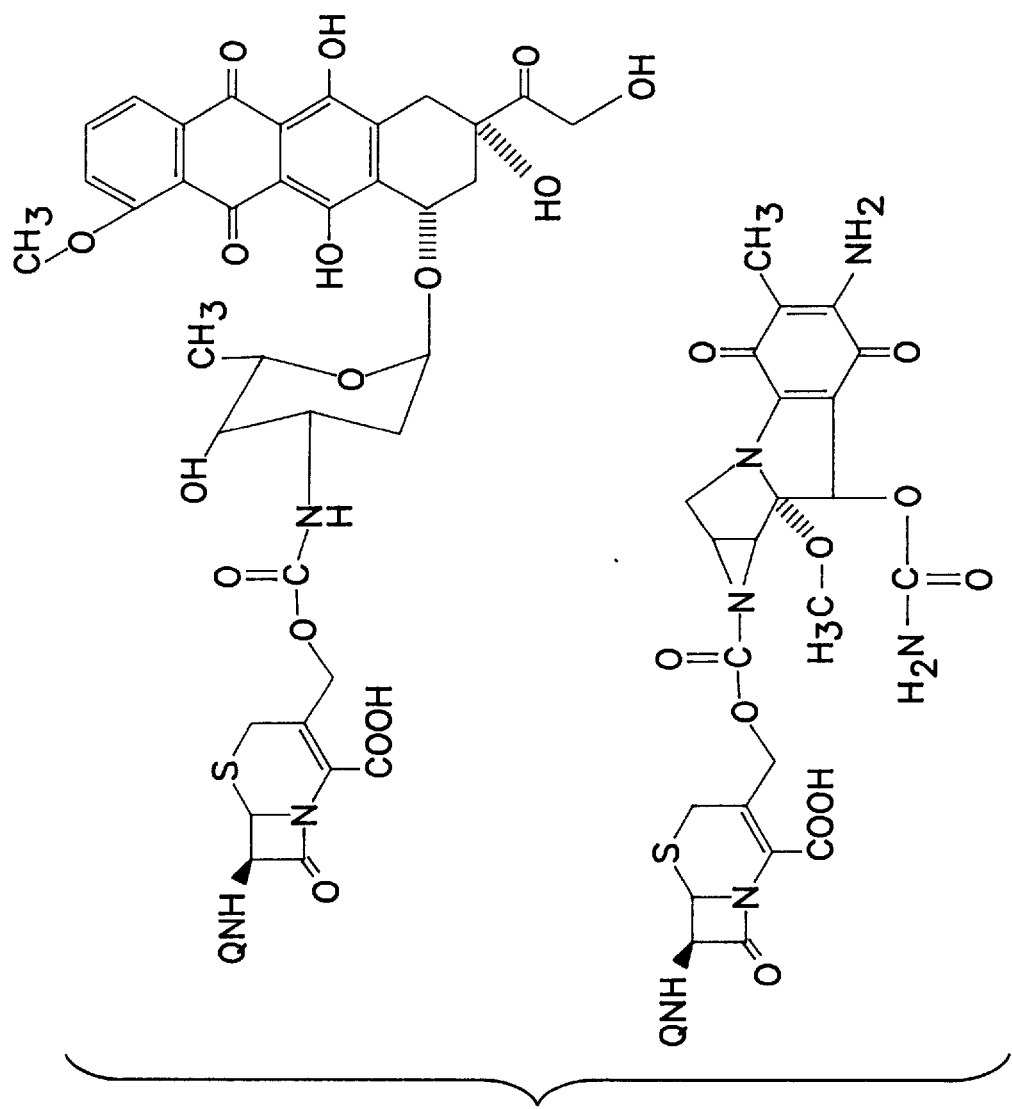
FIG. IA

PRODRUGS FOR β-LACTAMASE AND USES THEREOF

CROSS REFERENCE

This application is a continuation of application Ser. No. 07/770,371, filed Oct. 8, 1991, now abandoned, which is a continuation-in-part of application Ser. No. 07/609,663, filed Nov. 6, 1990, now abandoned, which is a continuation-in-part of application Ser. No. 07/211,301, filed Jun. 29, 1988, now U.S. Pat. No. 4,975,278 issued Dec. 4, 1990, which is a continuation-in-part of application Ser. No. 07/161,068, filed Feb. 26, 1988, now abandoned, which is a continuation-in-part of application Ser. No. 07/081,382, filed Aug. 4, 1987 and now abandoned; the content of all of said applications is incorporated herein by reference.

DESCRIPTION

1. Technical field

The instant invention relates generally to novel prodrugs and a method for delivering these prodrugs to a tumor cell site where they are converted to active cytotoxic agents. More particularly, the invention relates to cephalosporin prodrugs, which when administered with a tumor-specific-antibody-β-lactamase conjugate, are converted at the tumor site to active cytotoxic drugs.

2. Background

Targeted drug delivery systems provide a mechanism for delivering cytotoxic agents directly to cancerous cells. The selective delivery of cytotoxic agents to tumor cells is desirable because systemic administration of these agents often kills normal cells within the body as well as the tumor cells sought to be eliminated. Antitumor drug delivery systems currently in use typically utilize a cytotoxic agent conjugated to a tumor-specific antibody to form an immunoconjugate. This immunoconjugate binds to tumor cells and thereby "delivers" the cytotoxic agent to the site of the tumor. The immunoconjugates utilized in these targeting systems include antibody-drug conjugates (see, e.g., Baldwin et al., *Lancet*, pp. 603–605, Mar. 15, 1986) and antibody-toxin conjugates (see, e.g., Thorpe, in *Monoclonal Antibodies '84: Biological and Clinical Applications*, A. Oinchera et al., eds., pp 475–506, 1985).

Both polyclonal antibodies and monoclonal antibodies have been utilized in these immunoconjugates (see, e.g., Ohkawa et al., *Cancer Immunol. Immunother.* 23: 81, 1986; Rowland et al., *Cancer Immunol. Immunother.*, 21: 183, 1986). Drugs used in these immunoconjugates include daunomycin (see, e.g., Gallego et al., *Int. J. Cancer*, 33: 737, 1984; Arnon et al., *Immunological Rev.*, 62: 5, 1982; mexotrexate (Endo et al., *Cancer Research*, 47: 1076, 1987), mitomycin C (Ohkawa et al., supra), and vindesine (Rowland et al., supra). Toxins used in the antibody-toxin conjugates include bacterial toxins such as ricin (see e.g., Moolten et al., *Immunol. Rev.*, 62: 47, 1982).

Despite the amount of research directed towards the use of immunoconjugates for therapeutic purposes, several limitations involved in these delivery approaches have become apparent (see, e.g., Embleton, *Biochem. Society Transactions*, 14: 393, 615th Meeting, Belfast, 1986). For example, the large amount of drug required to be delivered to the target tumor cell to effect killing of the cell is often unattainable because of limitations imposed by the number of tumor-associated antigens on the surface of the cells and the number of drug molecules that can be attached to any given antibody molecule. This limitation has led to the use of more potent cytotoxic agents such as plant toxins in these conjugates and to the development of polymer-bound antibody-drug conjugates having very high drug multiplicity ratios (see, e.g., Thorpe, supra, pp. 475–506, and Baldwin et al., in *Monoclonal Antibodies and Cancer Therapy*, pp. 215–231, Alan R. Liss, Inc., 1985). However, even with the large drug loading ratios or with the use of potent toxins, many immunoconjugates still display suboptimal cytotoxic activity and are unable to effect complete killing at doses where all available antigenic sites are saturated.

It has also been recognized that the cytotoxic activity of an immunoconjugate is often dependent on its uptake, mediated by the antibody component of the conjugate into the tumor cell (see, e.g., J. M. Lambert et al., *J. Biol. Chem.*, 260: 12035, 1985). This internalization is crucial when using an antibody-drug conjugate in which the drug has an intracellular site of action or when using antibody-toxin conjugates. However, the vast majority of tumor-associated antigens and thus the antibody-drug or antibody-toxin conjugates bound to those antigens, are not internalized. Those conjugates that are internalized are often transported to the lysosome of the cell where the drug or toxin is degraded (see Vitetta et al., *Science*, 238: 1098, 1987). Accordingly, although an antibody-drug or antibody toxin conjugate may have excellent tumor-binding characteristics, the conjugate may nonetheless have a limited cytotoxic utility due to an inability to reach its site of action within the cell.

In addition, it is well established that tumor cell populations are often heterogeneous with respect to antigen expression (see, e.g., Albino et al., *J. Exp. Med.*, 154: 1764, 1981). Furthermore, it has been demonstrated that antigen-positive tumor cells may give rise to antigen-negative progeny (see, e.g., Yeh et al., *J. Immunol*, 126: 1312, 1981). Thus, in any population of tumor cells, there will be a certain number of cells that do not possess the antigen for which a particular immunoconjugate is specific. The immunoconjugate will therefore not be able to bind to these cells and mediate their killing.

Due to these drawbacks, the currently utilized antitumor drug or toxin delivery systems have had a limited amount of success, especially when used for in vivo treatment.

In addition to the immunoconjugates discussed above, antibody-enzyme conjugates have been studied in vitro in combination with a second untargeted enzyme for the conversion of iodide or arsphenamine to their toxic forms in order to amplify antibody-mediated cytotoxicity (see, e.g., Parker et al., *Proc. Natl. Acad. Sci. U.S.A.*, 72: 338, 1975; Philpott et al., *Cancer Research*, 34: 2159, 1974).

According to these in vitro studies, the enzyme, glucose oxidase, is attached to an antibody and used in combination with an untargeted peroxidase enzyme to convert iodide or arsphenamine to cytotoxic iodine or arsenical, respectively. This approach, therefore, requires not only the targeting of glucose oxidase to tumor cells with antibody, but also the presence at the tumor site of two other untargeted events. The likelihood that all three of these agents will be present in vivo at the tumor site at the same time is small.

Canadian Patent No. 1,216,791, discloses the conjugation to an antibody of an enzyme capable of liberating ammonium ions from substrates. The ammonium ions are then said to potentiate the cytotoxic action of certain immunotoxins targeted to the tumor site.

European Patent Application No. 84302218.7 discloses a method for treating a diseased cell population such as a tumor wherein an antibody is used to target a nonmetabolizable antigen to tumor cells. The antigen accumulates within at least a percentage of the tumor cells, which are then lysed to release the antigen into a ubiquitous fibronectin capturing matrix formed at the tumor site. An iodine-containing ligand which is specific for and will bind to the antigen affixed to the matrix is administered. The cytotoxic iodine acts to kill the tumor cells at that site. Also suggested is the use of an antibody-conjugate to target enzyme to a tumor site and the addition of a non-lethal substrate which the enzyme can convert to a cytotoxic material (see European Application No. 84302218.7, pp. 34–35). However, nowhere in the application is there any disclosure of how one is perform this embodiment. Similarly, Hellstrom et al., in *Controlled Drug Delivery* (2d ed.), Robinson and Lee (eds.) p. 639, 1987, suggest that "drugs which would be nontoxic until activated by an agent (e.g., an enzyme) localized to a tumor may be another approach. . . ."

U.S. Pat. No. 4,975,278, hereby incorporated by reference in its entirety, provides a method for delivering cytotoxic agents to tumor cells by the combined use of antibody-enzyme conjugates and prodrugs. According to this invention, an enzyme that is capable of converting a poorly or non-cytotoxic prodrug into an active cytotoxic drug is conjugated to a tumor-specific antibody. This antibody-enzyme conjugate is administered to a tumor-bearing mammalian host and binds, due to the antibody specificity, to the surface of those tumor cells which possess the tumor antigen for which the antibody is specific. The prodrug is then administered to the host and is converted at the tumor site by the action of the antibody-bound enzyme into a more active cytotoxic drug.

Nitrogen mustards have long been recognized as cytotoxic agents (See, e.g., Stock, in *Drug Design,* E. J., Ariens, ed., Vol. II, pp. 532–571, Academic Press, New York, 1971.) Benn, et al., *J. Chem. Soc.,* 2365 (1961) prepared a variety of amides, including urethanes and ureas, from N,N-di-2'-chloroethyl-para-phenylenediamine that are useful for reactions with various functional groups that are of potential value for the attachment of nitrogen mustards to a wide variety of other units. The attachment of the electron-attracting urethane group deactivates the highly toxic nitrogen mustard. Reactivation of the nitrogen mustard at the tumor site may occur if the urethane is decomposed by fission of the ester or peptide linkage.

Mobashery, et al. (*J. Am. Chem. Soc.,* 108:1685, 1986) teaches the use of β-lactamases resident in bacteria resistant to the β-lactam antibiotics, to hydrolyze cephalosporin-toxophore derivatives to effect the release of the toxophore within the bacterium.

Mobashery et al., (*J. Biol. Chem.,* 261: 7879, 1986) synthesized an antibacterial agent consisting of the antibiotic peptide βCl-LAla-βCl-LAla linked through a C$_{10}$ ester to the cephem nucleus of cephalosporin. The hydrolytic cleavage of the β-lactam ring by β-lactamase resident in the bacterium releases the heteroatom-linked C10 substituent.

A general discussion of the chemistry of the cephalosporins is provided by Abraham, *Quarterly reviews—Chemical Society,* 21:231, 1967, and Abraham et al., in *Cephalosporins and Penicillins: Chemistry and Biology,* E. H. Flynn, ed., Academic Press, N.Y., 1972, pp 1–26.

U.S. Pat. No. 3,484,437 teaches derivatives of cephalosporanic acid formed by the reaction of a deacylated cephalosporin salt with isocyanates to form carbamates.

U.S. Pat. No. 3,355,452 teaches the 0-desacetyl-O-carbamoyl-7-acylamino-cephalosporanic acid derivatives of 7-amino-cephalosporanic acid, where the 7-N-acyl group is a carboxylic acid radical and the CO group is bonded to a carbon atom.

DISCLOSURE OF THE INVENTION

The present invention is based on the discovery of novel cephalosporin-related prodrugs, capable of conversion to antitumor agents at the tumor site using a β-lactamase-antibody conjugate. The antibody is directed against a tumor antigen present on the surface of the specific tumor type targeted.

The present invention provides cephalosporin prodrugs of the general formula (I)

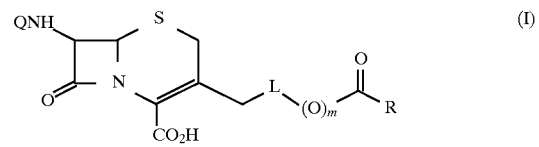

wherein Q is hydrogen, an amine protecting group conventionally used in cephalosporin synthesis, or the acyl group of a known 7-acylaminocephalosporin antibiotic; L is a direct bond or —S—(CH$_2$)$_n$—; R is an agent capable of exerting a cytotoxic effect on tumor cells when released from said cephalosporin-prodrug; n is 2, 3, or 4; and m is 0 or 1 with the proviso that when L is a direct bond, m is 1; or a pharmaceutically acceptable salt thereof.

For the purpose of the present invention, the nature of the substituent Q is not critical as the cephalosporin moiety serves as a carrier of the cytotoxic drug and does not contribute to the therapeutic effect of the cytotoxic drug. Thus, Q may be, for example, hydrogen, a protecting group commonly used in cephalosporin chemistry, or a substituent of known cephalosporin antibiotics. Examples of the latter include, but are not limited to, phenylacetyl, 2-thienylacetyl, α-hydroxyphenylacetyl, phenylglycyl, p-hydroxyphenylglycyl, and (2-amino-4-thiazolyl)-(methoxyimino)acetyl.

The cytotoxic compound is one having at least one functional group amenable to chemical modification to provide the cephalosporin prodrug. Generally, such functional groups are selected from amino, carboxyl, and hydroxyl groups such that the linkage between the cytotoxic agent and the cephalosporin component is of the carbamate, amide, ester, and carbonate types.

In one aspect, the present invention provides as one subclass of compounds of formula (I) cephalosporin prodrugs of the general formula (II) in which the cytotoxic agent is linked to the cephalosporin nucleus via carbamate or amide group

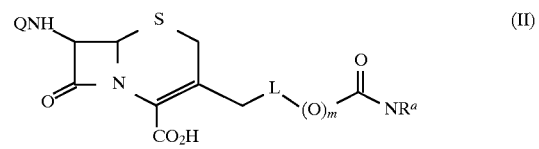

wherein Q, L, and m are as defined under formula (I); and NR$^a$ is a nitrogen containing cytotoxic drug; or a pharmaceutically acceptable salt thereof.

In another aspect the present invention provides a cephalosporin-mitomycin prodrug having the formula (IIa)

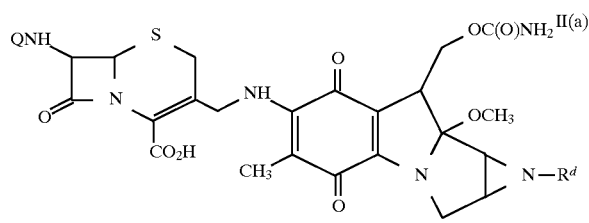

wherein Q is as defined above under formula (I) and $R^d$ is hydrogen or $C_{1-3}$ alkyl.

Another embodiment of the subject invention is directed to a method for delivering a cytotoxic agent to tumor cells by administering a pharmaceutically is effective amount of at least one antibody-β-lactamase conjugate comprising an antibody reactive with an antigen on the surface of the tumor cells. A pharmaceutically effective amount of a cephalosporin prodrug is also administered, where the cephalosporin prodrug comprises cephalosporin linked to the cytotoxic agent.

In an alternative embodiment, the present invention is directed to a method of delivering a cytotoxic agent to tumor cells wherein the antigen binding region of an antibody reactive with a tumor-associated antigen is linked to at least a functionally active part of β-lactamase, and is administered with a pharmaceutically effective amount of a cephalosporin prodrug.

In another embodiment, the subject invention is directed to a method of treating mammalian tumors which includes the step of administering to a mammal a pharmaceutically effective amount of at least one antibody-β-lactamase conjugate and a pharmaceutically effective amount of at least one cephalosporin prodrug.

These and other embodiments of the present invention will readily occur to those of ordinary skill in the art in view of the disclosure herein.

DETAILED DESCRIPTION

Figure 1B:
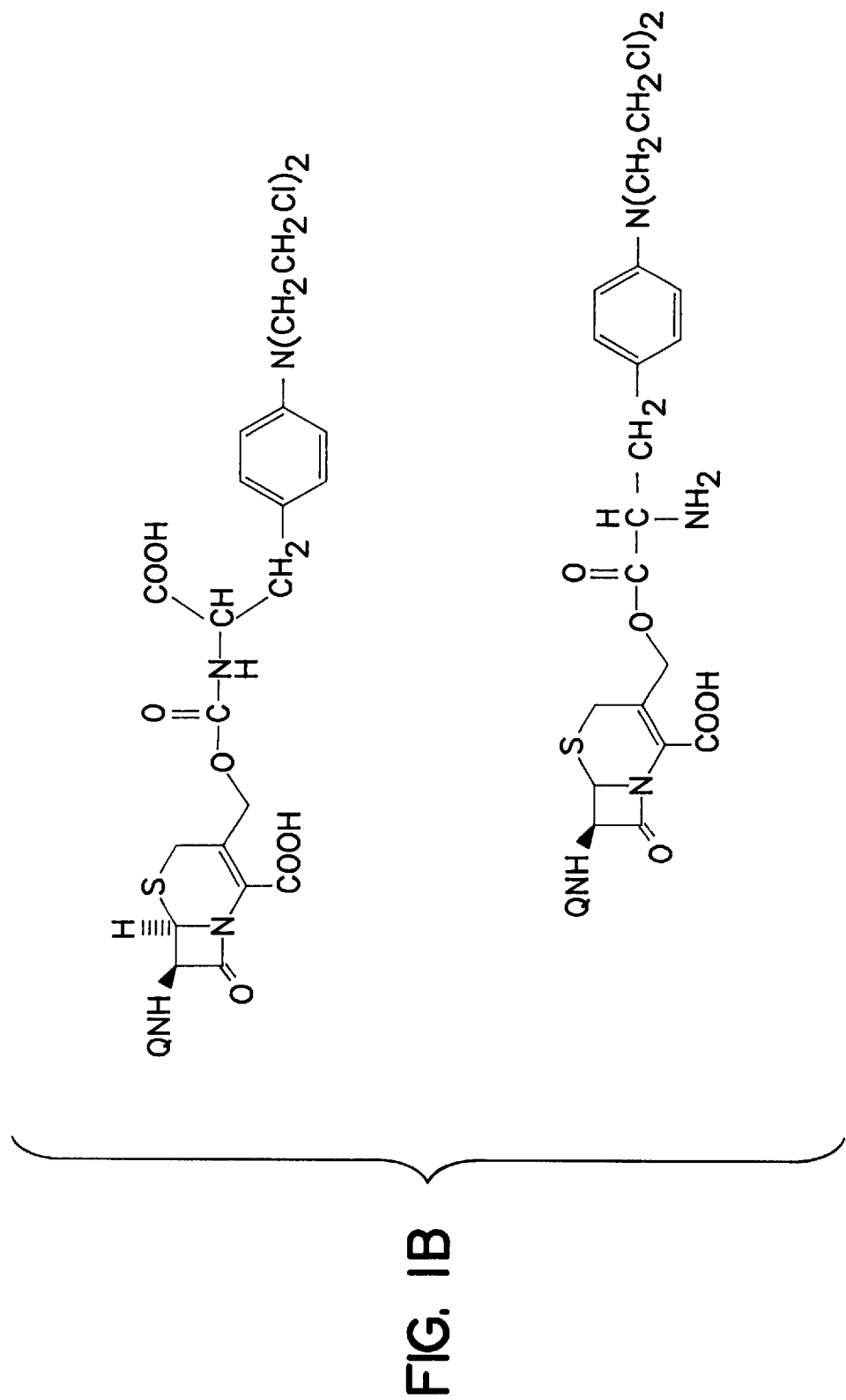
FIG. 1 depicts novel prodrug structures according to the instant invention. Q is phenylacetyl or thienylacetyl; n is 1 or 2.

The practice of the present invention will employ, unless otherwise indicated, conventional techniques of synthetic organic chemistry, protein chemistry, molecular biology, microbiology, and recombinant DNA technology, which are within the skill of the art. Such techniques are explained fully in the literature. See, e.g., Scopes, R. K., *Protein Purification Principles and Practices*, 2d ed. (Springer-Verlag, 1987), *Methods in Enzymology* (S. Colowick and N. Kaplan, eds., Academic Press, Inc.), Sambrook et al., *Molecular Cloning: A Laboratory Manual*, 2d ed., Cold Spring Harbor Press, Cold Spring Harbor, N.Y., 1989, *Handbook of Experimental Immunology*, Vols. I–IV (D. M. Weir and C. C. Blackwell, eds, 1986, Blackwell Scientific Publications); House, *Modern Synthetic Reactions*, 2nd ed., Benjamin/Cummings, Menlo Park, Calif., 1972.

All patents, patent applications, and publications mentioned herein, whether supra or infra, are hereby incorporated by reference in their entirety.

A. Definitions

In defining the present invention, the following terms will be employed, and are intended to be defined as indicated below.

The term "prodrug" as used in this application refers to a precursor or derivative form of a pharmaceutically active substance that is less cytotoxic to cells compared to the parent drug and is capable of being enzymatically activated or converted into the more active parent form. See, e.g, Wilman, *Biochem. Society Transactions*, 14:375 (615th Meeting, Belfast, 1986); Stella et al., *Directed Drug Delivery*, R. Borchardt et al., ed., 247–267 (Humana Press, 1985). The terms "parent drug" and "cytotoxic agent" are used interchangeably herein.

The term "cephalosporin prodrug" as used herein refers to a prodrug generated by the linkage of a parent compound as described above to a cephalosporin as defined below.

The term "β-lactamase" as used herein refers to any enzyme capable of hydrolyzing the CO—N bond of a β-lactam ring. The β-lactamases are reviewed in Bush, *Antimicrobial. Agents Chemother.*, 33:259, 1989.

The term "nitrogen mustard" as used herein refers to a compound of the general structure $RN(CH_2CH_2Cl)_2$, where R may be an alkyl, aryl, or aralkyl group substituted with a functional group amenable to further chemical modification, for example, an amino or a carboxyl group. Nitrogen mustards having more than one nitrogen atom are also included, such that both chloroethyl groups need not be attached to the same nitrogen atom. In some nitrogen mustards, the chlorine atoms may be replaced with other halogen atoms, especially bromine. See, e.g., Stock, in *Drug Design*, E. J., Ariens, ed., Vol. II, pp. 532–571, Academic Press, New York, 1971.

The term "cephalosporin" as used herein refers to derivatives of 7-aminocephalosporanic acid having the characteristic β-lactam dihydrothiazine ring of cephalosporin C, occurring either naturally or synthetically. Examples of these derivatives and a review of the chemistry of the cephalosporins is given in Abraham, *Quarterly reviews—Chemical Society*, 21: 231, 1967. The term "cephem" is sometimes used herein to refer to a cephalosporin. The structure of cephalosporin C is shown below:

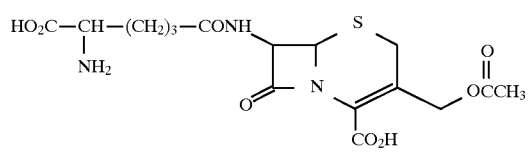

The term "cephalosporin mustard" as used herein refers to a cephalosporin as described above, wherein the cephalosporin has been derivatized with a nitrogen mustard as described above.

The term "cytotoxic" as used herein refers to the property of causing cell growth retardation or cell death, particularly as measured by a colony inhibition assay or $^3$H-thymidine uptake assay (see, eg., Hellstrom et al., in *In Vitro Methods in Cell-Mediated Immunity*, Bloom and Glade, eds., 1971, and the examples herein).

B. General Methods

The present invention relates to a novel method for the delivery of cytotoxic agents to tumor cells and provides for enhanced selective killing of tumor cells in the treatment of cancers, such as carcinomas and melanomas, as well as other tumors.

According to the method of the invention, an antibody-enzyme conjugate is administered to a tumor-bearing mammalian host. This antibody-enzyme conjugate consists of a tumor-selective antibody linked to a β-lactamase that is capable of converting a prodrug that is less cytotoxic to cells than the parent drug into the more active parent drug. When introduced into the host, the antibody component of the conjugate, which is reactive with an antigen found on the tumor cells, directs the conjugate to the site of the tumor and binds to the tumor cells. The antibody thus delivers the enzyme to the site of the tumor. A prodrug that is a substrate for the β-lactamase is also introduced into the host and is converted, at the tumor site, by the enzyme into an active cytotoxic drug. The drug is thus activated extracellularly and can diffuse into all of the tumor cells at that site, i.e., those cells bearing the particular tumor antigen to which the antibody of the conjugate is specific and to which the antibody has bound as well as those cells that are negative for that antigen but are nonetheless present at the site of the tumor. The method of this invention therefore overcomes the current problems of tumor antigen heterogeneity and the requirement of antigen/conjugate internalization associated with conventional immunoconjugate drug delivery techniques.

Furthermore, because the present method does not require the drug to be bound directly to the antibody and thereby limit the amount of drug that can be delivered, the commonplace problem of drug potency at the tumor site does not arise. In fact, the present method amplifies the number of active drug molecules present at the tumor site because the antibody-bound enzyme of the conjugate can undergo numerous substrate turnovers, repeatedly converting prodrug into active drug. Moreover, the present method is capable of releasing the active drug specifically at the tumor site as opposed to release to other tissues. This is so because the concentration of the enzyme at the tumor site is higher than its concentration at other tissues due to the coating of the tumor cells with the antibody-enzyme conjugate.

The antibody of the immunoconjugate of the invention includes any antibody which binds specifically to a tumor-associated antigen. Examples of such antibodies include, but are not limited to, those which bind specifically to antigens found on carcinomas, melanomas, lymphomas, and bone and soft tissue sarcomas as well as other tumors. Antibodies that remain bound to the cell surface for extended periods or that are internalized very slowly are preferred. These antibodies may be polyclonal or preferably, monoclonal, may be intact antibody molecules or fragments containing the active binding region of the antibody, e.g., Fab or F(ab')$_2$, and can be produced using techniques well established in the art. See, e.g., R. A. DeWeger et al., *Immunological Rev.*, 62: 29–45, 1982 (tumor-specific polyclonal antibodies produced and used in conjugates): Yeh et al., *Proc. Natl. Acad. Sci. U.S.A.*, 76:2927, 1979; Brown et al., *J. Immun.*, 127:539, 1981 (tumor-specific monoclonal antibodies produced); and Mach et al., in *Monoclonal Antibodies for Cancer Detection and Therapy*, R. W. Baldwin et al., eds., pp 53–64, Academic Press, 1985 (antibody fragments produced and used to localize tumor cells). In addition, if monoclonal antibodies are used, the antibodies may be of mouse or human origin or chimeric antibodies (see, e.g., Oi, *Biotechniques*, 4:214, 1986).

Examples of antibodies which may be used to deliver the β-lactamase to the tumor site include, but are not limited to, L6, an IgG2a monoclonal antibody (hybridoma deposit no. ATCC HB8677) that binds to a glycoprotein antigen on human lung carcinoma cells (Hellstrom, et al., *Proc. Natl. Acad. Sci. U.S.A.*, 83:7059, 1986); 96.5, an IgG2a monoclonal antibody that is specific for p97, a melanoma-associated antigen (Brown, et al., *J. Immunol.* 127:539, 1981); 1F5, an IgG2a monoclonal antibody (hybridoma deposit no. ATCC HB9645) that is specific for the CD-20 antigen on normal and neoplastic B cells (Clark et al., *Proc. Natl. Acad. Sci. U.S.A.*, 82:1766, 1985).

An alternative strategy is to use antibodies that internalize, providing that the prodrug can also internalize, or that a sufficient amount of antibody also remains on the surface of the cell. An example of such antibodies may be found in *Cancer Research* 56:2183 (1990).

The enzyme component of the immunoconjugate of the invention includes any enzyme capable of hydrolyzing the CO—N bond of a β-lactam. Some of these enzymes are available commercially, such as *E. coli* or *B. cereus* β-lactamases. These and other β-lactamases may be cloned and expressed using recombinant DNA techniques well known in the art.

The β-lactamases of this invention can be covalently bound to antibodies by techniques well known in the art such as the use of the heterobifunctional crosslinking reagents SPDP (N-succinimidyl-3-(2-pyridyldithio)propionate) or SMCC (succinimidyl 4-(N-maleimidomethyl) cyclohexane-1-carboxylate (see, e.g., Thorpe et al., *Immunol. Rev.*, 62: 119, 1982; Lambert et al., supra, at p. 12038; Rowland et al., supra, at pp 183–184; Gallego et al., supra, at pp. 737–7138). Alternatively, fusion proteins comprising at least the antigen binding region of an antibody linked to at least a functionally active portion of a β-lactamase can be constructed using recombinant DNA techniques well known in the art (see, e.g., Neuberger et al., *Nature*, 312:604, 1984). These fusion proteins act in essentially the same manner as the antibody-enzyme conjugates described herein.

The prodrugs of the invention contain an antitumor agent linked to a cephalosporin or cephalosporin derivative. The antitumor agent is activated or otherwise converted into a more active form upon cleavage of the prodrug with β-lactamase. In the preferred embodiment, the antitumor agent is a nitrogen mustard, as defined above. A representative nitrogen mustard is shown below:

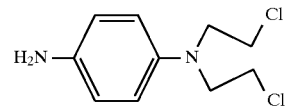

Other preferred antitumor agents include adriamycin, which has the general formula:

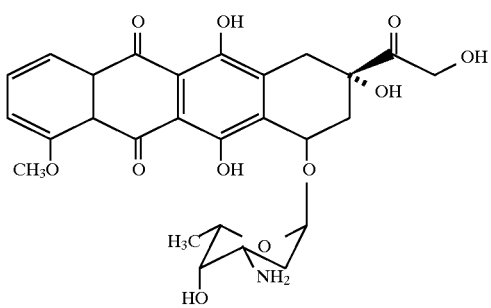

and mitomycin C, which has the general formula:

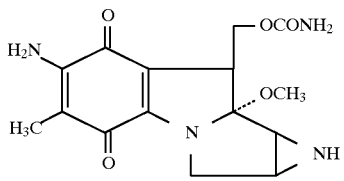

The prodrugs of this invention are not limited to these compounds, and may include other antitumor agents that can be derivatized into a prodrug form for use in a cephalosporin conjugate. Such antitumor agents include etoposide, teniposide, daunomycin, carminomycin, aminopterin, dactinomycin, cis-platinum and cis-platinum analogues, bleomycins, esperamicins (see U.S. Pat. No. 4,675,187), and 5-fluorouracil.

In one preferred embodiment of this invention, an anthracycline-cephalosporin prodrug is synthesized by reaction of an anthracycline with a carboxyl protected 3-[(carbonyloxy) methyl] cephem such as the diphenylmethyl esters of 3-[[(p-nitrophenoxy) carbonyloxy]methyl]cephem and 3-(1,2,2,2-tetrachloroethoxy) carbonyloxy]methyl] cephem. The resulting prodrug contains an anthracycline linked to the cephalosporin by the amino group of the former through a carbamate bond.

In another preferred embodiment of this invention, a cephalosporin mustard is synthesized by reaction of a 3-hydroxymethyl cephalosporin salt with an isocyanate, as described in U.S. Pat. Nos. 3,355,452, and 3,484,437, and Belgian Patent No. 741,381, herein incorporated by reference in their entirety. Such a reaction is also described in detail in the examples.

More generally, the present invention provides cephalosporin prodrugs of the general formula (I)

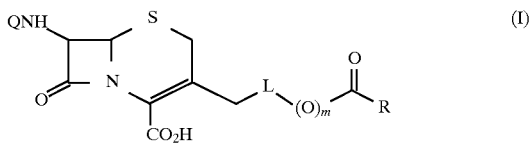

wherein Q is hydrogen, an amine protecting group conventionally used in cephalosporin synthesis, or the acyl group of a known 7-acylaminocephalosporin antibiotic; L is a direct bond or —S—$(CH_2)_n$—; R is an agent capable of exerting a cytotoxic effect on tumor cells when released from said cephalosporin-prodrug; n is 2, 3, or 4; and m is 0 or 1 with the proviso that when L is a direct bond, m is 1; or a pharmaceutically acceptable salt thereof.

For the purpose of the present invention, the nature of the substituent Q is not critical as the cephalosporin moiety serves as a carrier of the cytotoxic drug and does not contribute to the therapeutic effect of the cytotoxic drug. Thus, Q may be, for example, hydrogen, a protecting group commonly used in cephalosporin chemistry, or a substituent of known cephalosporin antibiotics. Examples of the latter include, but are not limited to, phenylacetyl, 2-thienylacetyl, α-hydroxyphenylacetyl, phenylglycyl, p-hydroxyphenylglycyl, and (2-amino-4-thiazolyl)-(methoxyimino)acetyl.

"An amino protecting group" of the sort conventionally used in cephalosporin synthesis includes, but is not limited to, lower alkanoyl or substituted lower alkanoyl, e.g. formyl, acetyl, chloroacetyl, and trifluoroacetyl; aroyl or substituted aroyl, e.g. benzoyl, 4-methoxybenzoyl, and 4-nitrobenzoyl; aralkyl, substituted aralkyl, aralkylidene, or substituted aralkylidene, e.g. benzyl, diphenylmethyl, trityl, nitrobenzyl, methoxybenzyl, and benzylidene; halogenated alkyl, e.g. trichloromethyl, trichloroethyl, and trifluoromethyl; alkoxycarbonyl or substituted alkoxycarbonyl, e.g. methoxycarbonyl, ethoxycarbonyl, t-butoxycarbonyl, cyclohexyloxycarbonyl, and trichloroethoxycarbonyl; aralkoxycarbonyl or substituted aralkoxycarbonyl, e.g. benzyloxycarbonyl, methoxybenzyloxycarbonyl, and nitrobenzyloxycarbonyl; an unsubstituted or substituted trialkylsilyloxycarbonyl or triarylsilyloxycarbonyl; and trialkylsilyl or triarylsilyl groups, e.g. trimethylsilyl and t-butyldimethylsilyl.

"Acyl group of a known 7-acylaminocephalosporin antibiotic" refers to the substituent on the 7-amino group of a known cephalosporin antibiotic and may be represented by the formula R—C(O)—. Examples of R include, but are not limited to, (a) 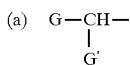

wherein G may be a substituted or unsubstituted aryl, heterocyclic, or cyclohexadienyl group, e.g. phenyl, thienyl, thiazolyl, thiadiazolyl, imidazolyl, pyridyl, tetrazolyl, 1,4-cyclohexadienyl, and furyl; the substituents for the groups may be 1 to 3 of the same or different groups selected from halogen, hydroxy, amino, alkoxy, alkylamino, dialkylamino, alkanoyloxy, carboxy, nitro, cyano, and alkoxycarbonyl; G' may be hydrogen, hydroxy, amino, monoalkylamino, dialkylamino, alkanoylamino, alkanoyloxy, carboxy, and sulfo;

(b) 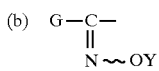

wherein G has the same meaning given above, and Y is hydrogen, $C_{1-6}$alkyl, or $C_{1-6}$alkanoyl;

(c) G—B—$CH_2$— wherein G has the same meaning given above, and B is oxygen or sulfur; and (d) 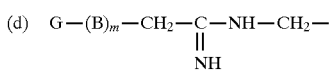

where G, and B have the meanings given above, and m is 0 or 1.

Some specific examples of "acyl group of a known 7-acylaminocephalosporin antibiotic" include 2-amino-2-phenylacetyl, 2-amino-2-(4-hydroxy)phenylacetyl, 2-thienylacetyl, phenylacetyl, 2-hydroxy-2-phenylacetyl, 2-acetoxy-2-phenylacetyl, 1-tetrazolylacetyl, [(2-amino-4-thiazolyl)(methoxyimino)]acetyl, glutaroyl phenoxyacetyl, and [(2-furanyl)(methoxyimino)]acetyl.

The cytotoxic compound is one having at least one functional group amenable to chemical modification to provide the cephalosporin prodrug. Generally, such functional groups are selected from amino, carboxyl, and hydroxyl groups such that the linkage between the cytotoxic agent and the cephalosporin component is of the carbamate, amide, ester, and carbonate types.

In one aspect, the present invention provides as one subclass of compounds of formula (I) cephalosporin prodrugs of the general formula (II) in which the cytotoxic agent is linked to the cephalosporin nucleus via carbamate or amide group solvent to afford compounds of formula (V). Alternatively, a carboxyl-protected cephalosporin carbonate of formula (IV) is treated with a nitrogen containing cytotoxic agent followed by deprotection of the carboxyl group to provide the desired cephalosporin prodrug (V). The cephalospbrin carbonate (IV) may, in turn, be prepared from a carboxyl-protected 3-hydroxymethyl cephalosporin upon reaction with a chloroformate, e.g., 4-nitrophenyl chloroformate and 1,2,2,2-tetrachloroethyl chloroformate. In Scheme I, Q and $NR^a$ have the same meaning as defined under formulas (I) and (II), $R^1$ is an ester activating group, preferably 4-nitrophenyl, or 1,2,2,2-tetrachloroethyl; and $R^2$ is a carboxyl protecting group, for example, benzyl, t-butyl, diphenylmethyl, allyl and the like. The carboxyl protecting group may be removed using conventional techniques such as acid catalyzed hydrolysis and reductive palladium catalysis.

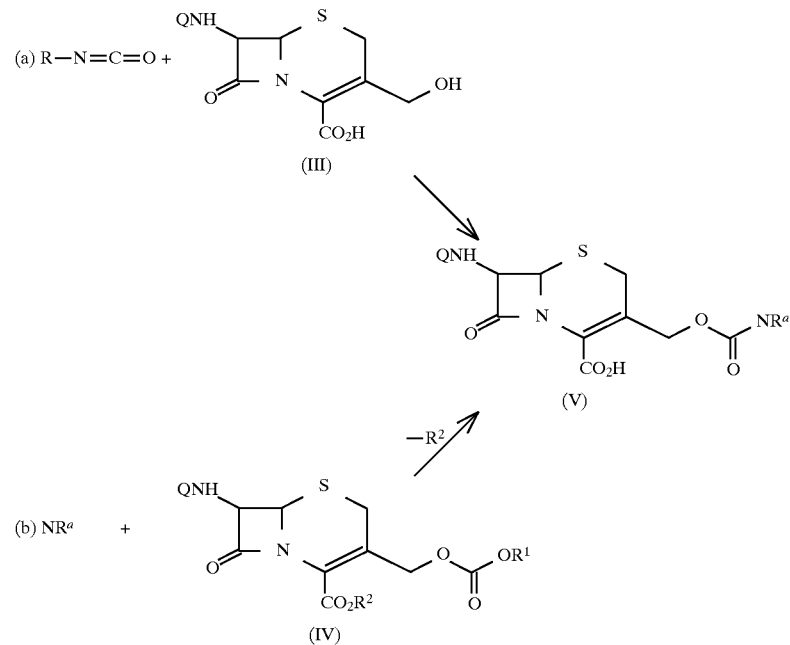

Scheme I

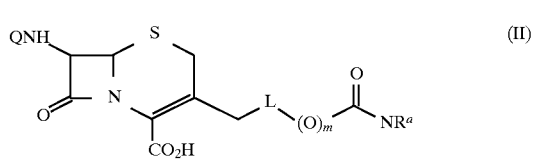

(II)

wherein Q, L, and m are as defined under formula (I); and $NR^a$ is a nitrogen containing cytotoxic drug; or a pharmaceutically acceptable salt thereof.

Compounds of formula (II) wherein L is a direct bond may be prepared by reaction sequences illustrated in Scheme I. Thus, a 3-hydroxymethyl cephalosporin (III), preferably in an alkali metal salt form such as the sodium or potassium salt, is reacted with an isocyanato derivative of a cytotoxic agent in the presence of a tertiary amine base in an aprotic Compounds of formula (II), wherein L is $-S-(CH_2)_n-$ and m is 1, may be prepared by a method analogous to route (b) of Scheme I. The preparation of the cephalosporin reactant (VI) and its subsequent elaboration to yield the cephalosporin prodrug of formula (VII) is illustrated in Scheme II. In Scheme II, Q, NR, n, $R^1$, and $R^2$ all have the same meaning as previously defined; X is a halogen atom such as chloro, bromo or iodo. The starting cephalosporin of formula (VI) may be prepared by reacting a carboxyl protected 3-halomethyl cephalosproin of formula (VIII) with a mercaptoalkanol, and the resulting 3-hydroxyalkylthiomethyl cephalosporin is treated with a chloroformate $ClCO_2R^1$, e.g., 4-nitrophenylchloroformate in the presence of a tertiary amine base to afford the compound of formula (VI).

Scheme II
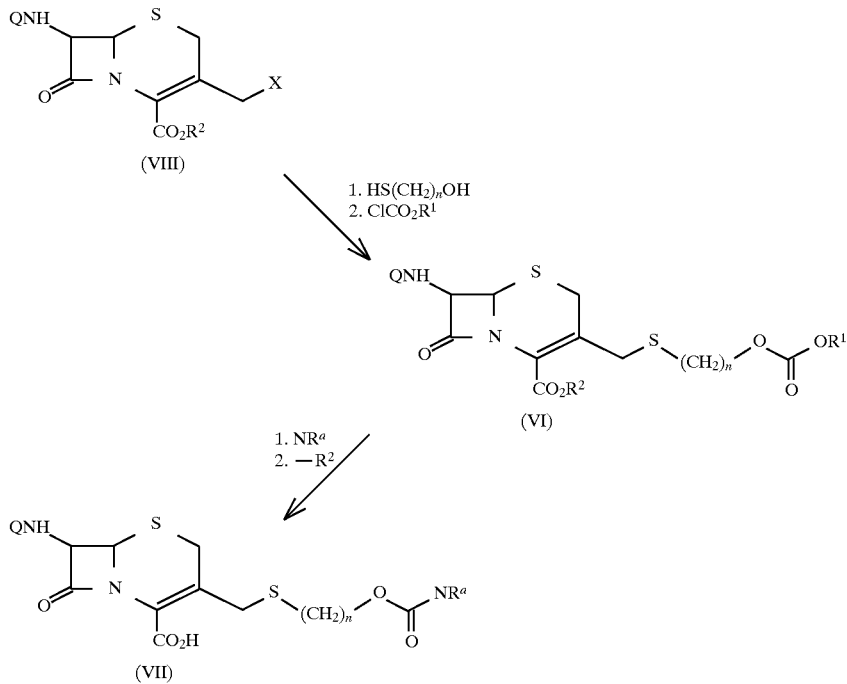
Compounds of formula (II), wherein L is —S—(CH$_2$)$_n$— and m is 0, may be prepared by methods illustrated in Scheme III.
In Scheme III, Q, NR$^a$, n, X, R$^1$, and R$^2$ have the same meaning as previously defined. Thus, a nitrogen containing cytotoxic agent is reacted with a 3-thioalkylcarboxylate
Scheme III
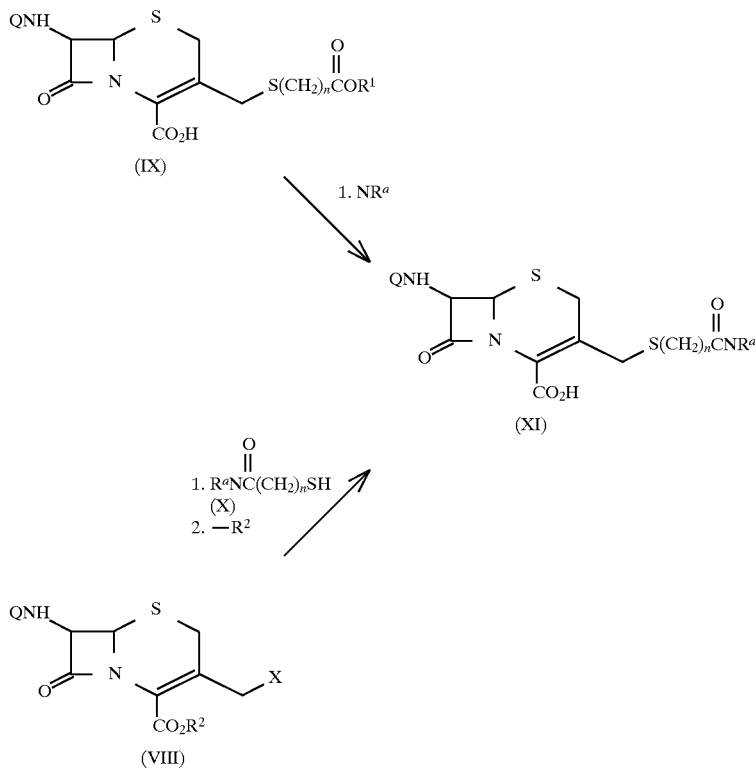

substituted cephalosporin derivative (IX) to form the resulting carbamate prodrug of formula (XI). The cephalosporin derivative of formula (IX) in turn may be obtained by reacting a thioalkylcarboxylate, $HS(CH_2)_nCO_2R^1$, with a 3-halomethyl cephalosporin, or by reaction a carboxyl protected 3-halomethyl cephalosporin with a thioalkanoic acid followed by activation of the acid moiety. For example, $R^1$ of compound (IX) may be succinimide or the group —$CO_2R^1$ may represent a mixed anhydride.

Alternatively, the cytotoxic agent may first be derivatized to form the N-thioalkylcarbonyl compound of formula (X) by reacting $NR^a$ with a thioalkylcarboxylate, $HS(CH_2)_nCO_2R^1$. Compound (X) is then reacted with a carboxyl-protected 3-halomethyl cephalosporin (VIII) to give the desired product. For the preparation of compounds of formula (XI), $R^1$ may be, for example, succinimide, or —$CO_2R^1$ may represent a mixed anhydride).

The cytotoxic drug component $NR^a$ may be a member of the nitrogen mustard family as defined above. Particularly preferred mustards are melphalan and N,N-bis(2-chloroethyl)-1,4-benzenediamine (phenylenediamine mustard). In addition, the cytotoxic drug component $NR^a$ may be a member of the anthracyline family. Examples of anthracyclines include, but are not limited to, adriamycin, daunomycin, carminomycin, and the like in which the linkage to the cephalosporin is via the sugar amino group. Preferably, the anthracycline is adriamycin.

The cytotoxic drug component $NR^a$ may also be a member of the mitomycin family. Mitomycins are characterized by the following general structure:

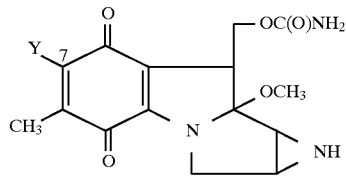

A large number of mitomycin analogs having different substituents on the 7-position have been reported. For the purpose of the present invention, the 7-substituent is not critical as the linkage of the mitomycin to the cephalosporin is through the aziridine nitrogen atom. A preferred mitomycin for the prodrug is mitomycin C, i.e., Y=$NH_2$. Other examples of mitomycin analogs suitable for the present prodrug may be those disclosed in U.S. Pat. Nos. 4,691,023, 4,803,212, 4,487,769, 4,888,341, and European Published Application 294,828, hereby incorporated by reference.

In another aspect, the present invention provides as a subclass of compounds of formula (I) cephalosporin prodrugs of the general formula (XII) in which the cytotoxic agent is linked to the cephalosporin nucleus via a carbonate or an ester group

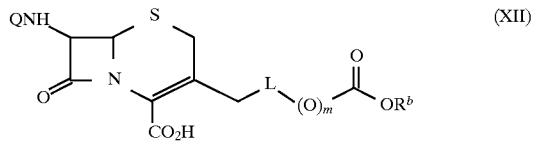

wherein Q, L, and m are as previously defined; $OR^b$ is a hydroxy containing cytotoxic drug; or a pharmaceutically acceptable salt thereof. Compounds of formula (XII) may be prepared according to the general methods described in Schemes I to III (with the exception of route (a) in Scheme I) using $OR^b$ instead of $NR^a$ used therein.

As one example of the present invention, the cytotoxic component $OR^b$ is selected from the group of epipodophyllotoxin antitumor agents having the formula

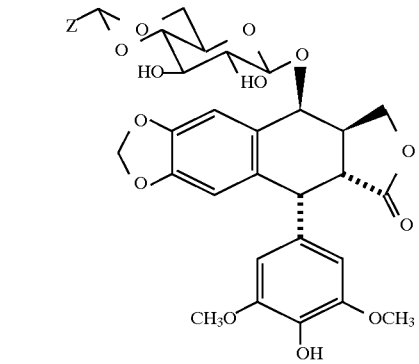

wherein Z is the substituent of a known epipodophyllotoxin glucoside, e.g., alkyl, thienyl, furyl, and phenyl. Particularly preferred are compounds wherein Z is methyl (etoposide) and 2-thienyl (teniposide). These compounds may be linked to the cephalosporin nucleus through the 4'-phenol group.

In another aspect, the present invention provides as a subclass cephalosporin prodrugs of the formula (XIII)

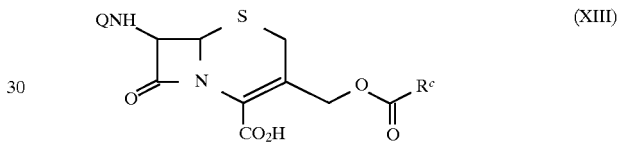

wherein Q is as previously defined; and $R^cCOO$ is a carboxy containing cytotoxic compound; or a pharmaceutically acceptable salt thereof.

As an example of this, the cytotoxic component melphalan may be linked to the cephalosporin nucleus via the carboxyl group. The melphalan-cephalosporin prodrug (XIV) may be prepared by the procedure depicted in Scheme IV.

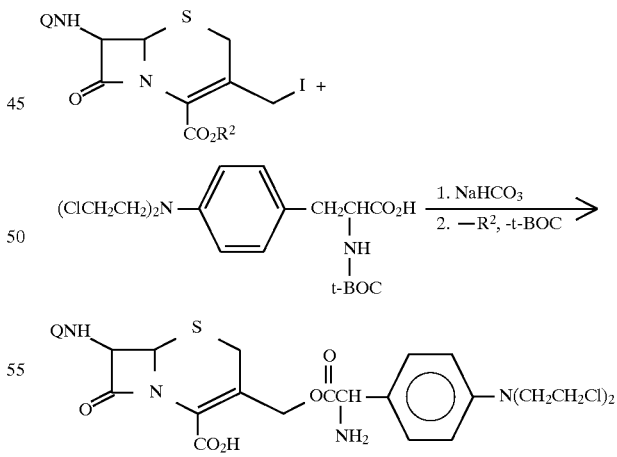

In Scheme IV, Q and $R^2$ are as previously defined. Preferably, $R^2$ is an acid labile group such as benzyl or t-butyl. t-BOC is the group t-butoxycarbonyl. Thus, carboxy-protected 3-iodocephalosporin is reacted with N-t-BOC protected melphalan in the presence of a base, e.g., sodium bicarbonate; the resulting diprotected intermediate is treated with an acid to afford the desired product of formula (XIV).

Figure 2:
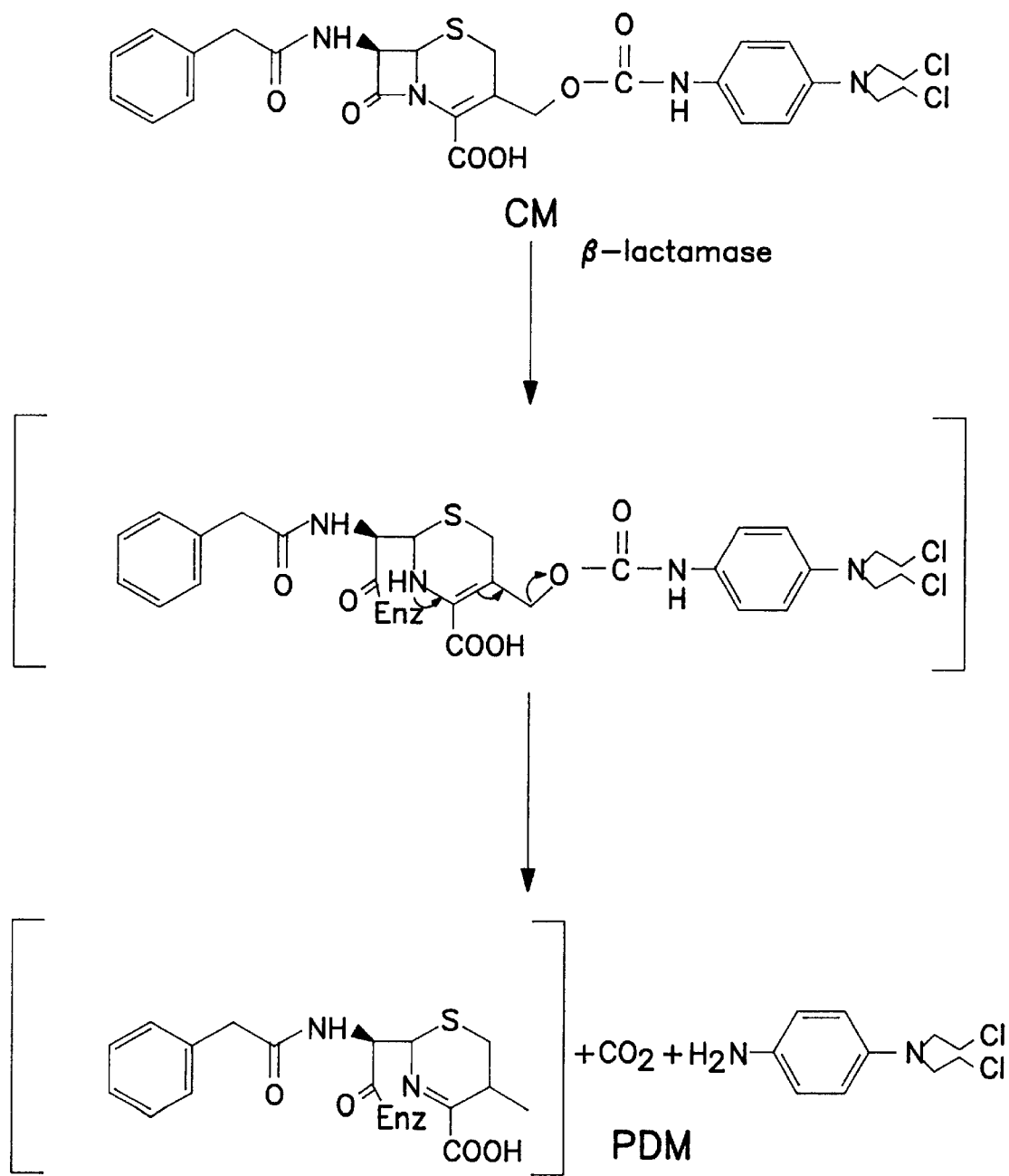
FIG. 2 depicts a representative cephalosporin mustard prodrug (CM) and the conversion of this prodrug to the active cytotoxic agent, phenylenediamine mustard (PDM).

A representative cephalosporin prodrug made according to the general procedure of route (a) in Scheme I is depicted in Equation (i). Specifically, 3-hydroxymethyl cephalosporin (1) is reacted with the isocyanate (2) to generate the cephalosporin mustard (3) (Equation i). As shown in FIG. 2, upon cleavage with β-lactamase, the cephalosporin mustard is hydrolyzed to generate the phenylenediamine mustard, PDM.

hereinabove but may be accomplished using other conventional techniques well known to a chemist skilled in the art of organic synthesis. The selection of protecting groups, ester activating groups (and their introduction and removal, if applicable), solvents, and reaction conditions is within the knowledge of a synthetic chemist and may be performed without undue experimentation.

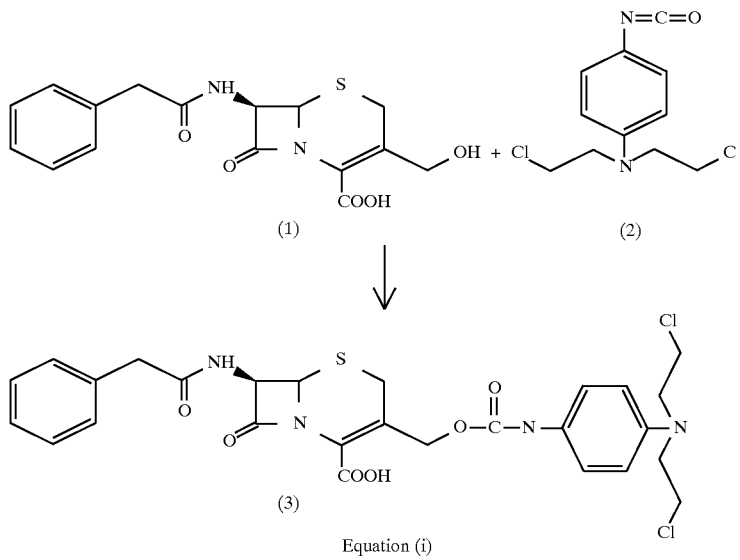

Equation (i)

Figure 1C:
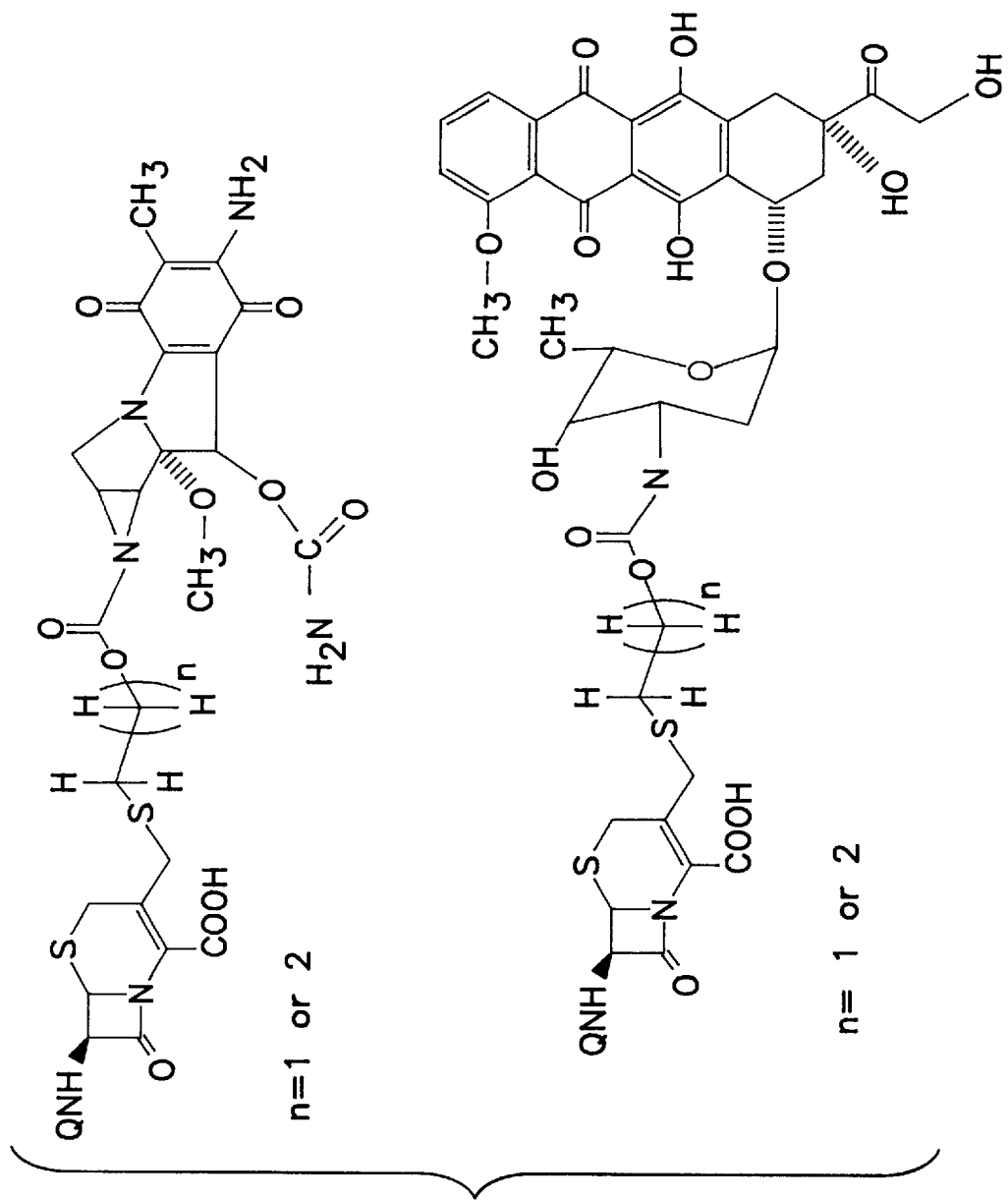
Figure 1D:
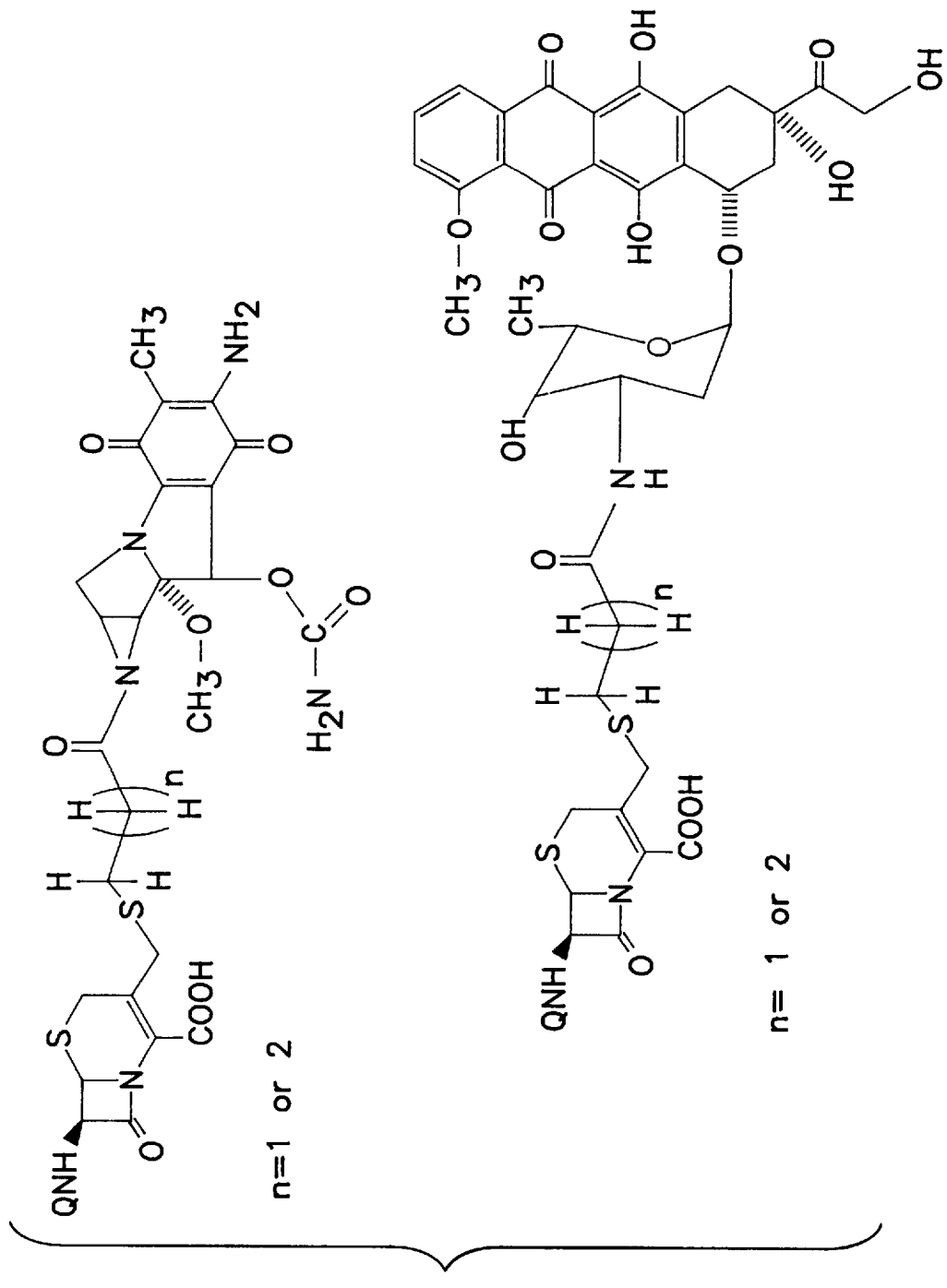

Other representative prodrugs for use in the instant invention are depicted in FIG. 1. These prodrugs shown in FIG. 1 may be synthesized in accordance with general procedures described in schemes I through IV. These techniques are well known by one of ordinary skill in the art.

Another aspect of the present invention concerns cephalosporin-mitomycin prodrugs having the formula (IIa)

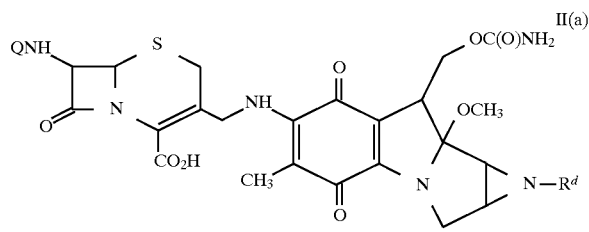

wherin Q and $R^d$ are as defined above. Compounds of formula (IIa) are prepared by reacting a 3-aminomethyl cephalosporin with mitomycin A or a $N^{1a}$-alkyl derivative thereof ($N^{1a}$ refers to the aziridine nitrogen of mitomycins). The reaction is conducted in an organic solvent, e.g. ethanol or methanol, at a temperature conducive to product formation, e g. at ambient temperature. The reaction is generally completed within 24 hours. Preferably, the reaction is carried out under inert atmosphere. The starting material 3-aminomethyl cephalosporin is obtained from the corresponding 3-azidomethyl cephalosporin; both the 3-aminomethyl- and the 3-azidomethyl cephalosporin and methods for their preparation are disclosed in Cocker, J. D. et al, *J. Chem. Soc.*, 1965, 5015 at 5027–5029, the relevant portions thereof are hereby incorporated by reference.

It will be appreciated that synthesis of the cephalosporin prodrugs encompassed by the present invention is not limited to those procedures and reagents specifically described The present invention also encompasses pharmaceutical compositions and methods for treating cancers and other tumors. More particularly, the invention includes compositions comprising cephalosporin prodrugs which are capable of being cleaved by antibody-β-lactamase conjugates. The prodrugs and enzyme conjugates are used in a method for treating tumors wherein a mammalian host is given a pharmaceutically effective amount of an antibody-enzyme conjugate or conjugates and a pharmaceutically effective amount of a prodrug or prodrugs. The compositions and methods of this invention are useful in treating any mammal, including humans, dogs, cats, and horses.

According to a preferred embodiment, the antibody-enzyme conjugate is administered prior to the introduction of the prodrug into the host. Sufficient time should be allowed between the administration of the conjugate and the prodrug to allow the antibody of the conjugate to target and localize the enzyme to the tumor site. The time may range from 12 hr to one week depending upon the conjugate used.

The conjugates and prodrugs of the invention can be administered using conventional modes of administration including, but not limited to, intravenous, intraperitoneal, oral, intralymphatic, or administration directly into the tumor. Intravenous administration is preferred.

The compositions of the invention may be in a variety of dosage forms which include, but are not limited to, liquid solutions or suspensions, tablets, pills, powders, suppositories, polymeric microcapsules or microvesicles, liposomes, and injectable or infusible solutions. The preferred form depends upon the mode of administration and the therapeutic application. For example, oral administration of the antibody-β-lactamase conjugate may be disfavored because the conjugate proteins tend to be degraded in the stomach if taken orally, e.g., in tablet form.

The conjugate or prodrug compositions also preferably include conventional pharmaceutically acceptable carriers and adjuvants known in the art such as human serum albumin, ion exchangers, alumina, lecithin, buffer substances such as phosphates, glycine, sorbic acid, potassium sorbate, and salts or electrolytes such as protamine sulfate.

The most effective mode of administration and dosage regimen for the compositions of this invention depends upon the severity and course of the disease, the patient's health and response to treatment and the judgment of the treating physician. Accordingly, the dosages of the immunoconjugates and prodrugs should be titrated to the individual patient. Methods of determining dosages are well known in the art.

Nevertheless, an effective dose of the antibody-enzyme conjugate of this invention will be in the range of from about 1.0 to about 1000 mg/M$^2$, the dose of the prodrug depending upon the particular prodrug used and the parent drug from which it is derived. Since the prodrug is less cytotoxic than the parent drug, dosages in excess of those recognized in the art for the parent drug may be used.

In order that the invention described herein may be more fully understood, the following examples are set forth. It should be understood that these examples are for illustrative purposes only and are not to be construed as limiting the scope of the invention in any manner.

C. Experimental
1. Preparation of Chemical Compounds
1.1 Preparation of intermediates
1.1.1 N,N-bis(2-chloroethyl)-4-isocyanato-benzenamine N,N-bis(2-chloroethyl)-4-isocyanato-benzenamine (4 g, 16.2 mmol, prepared according to the method of Everett et al., *J. Chem Soc.* 1949 (1972) was dissolved in 80 ml concentrated HCl and cooled in a water bath. Tin chloride trihydrate (6 g) was added in one portion and the reaction was allowed to stir for 10 min. The reaction was removed from the cooling bath and stirred for an additional 35 min. The tan solid product was collected by suction filtration on a glass fritted funnel and washed with 20 ml concentrated HCl. The tan solid was dissolved in 100 ml water and cooled in an ice bath. Cold 1N NaOH was added until the pH of the solution was 8. The cloudy white solution was extracted with 150 ml diethyl ether, washed with 80 ml saturated aqueous NaCl, and dried over anhydrous Na$_2$SO$_4$. Pyridine (2.7 ml) was added to the solution containing the drying agent. The solution was mixed and immediately filtered through glass wool directly into a stirring solution of Phosgene (8.4 ml of 1.93M in Toluene, Fluka Chem. Co.) in 50 ml diethyl ether at 2° C. A white solid formed. The reaction was stirred for 60 min at 2° C. and then for 15 min at ambient temperature. The reaction was filtered by suction and concentrated in vacuo to give the crude isocyanate (2.81 g) as a dark green viscous oil. The isocyanate prepared in this manner showed the characteristic stretch in the IR.

1.1.2 Potassium 3-(hydroxymethyl)-8-oxo-7-(phenylacetamido)-5-thia-1-azabicyclo[4.2.0]oct-2-ene-2-carboxylate A solution of sodium 3-(acetoxymethyl)-8-oxo-7-(phenylacetomido)-5-thia-1-azabicyclo[4.2.0]oct-2-ene-2-carboxylate (also known as cefaloram) was prepared by dissolving 8.5 g (20.6 mmol) of this salt in 55 ml water and 27 ml methanol and cooling to −10° C. The pH was adjusted to 11.5–12.0 by adding 2.0 ml 20% NaOH, then 5 ml 2:1 water/methanol. While still at −5° C., concentrated H$_3$PO$_4$ was added dropwise with vigorous stirring until no more precipitate formed. The resulting solution was poured into 900 ml ethyl acetate and 100 ml water. The mixture was extracted and the organic layer dried over anhydrous sodium sulfate. The solution was filtered into a vigorously stirred solution of 2 L EtOAc to which had been added a solution of 5 g potassium 2-ethyl hexanoate in 50 ml acetone. The resulting precipitate was filtered by suction and washed with EtOAc to yield a cream colored solid. The solid was dried for 12 hr at 60° C. over P$_2$O$_5$ under vacuum to provide 5.63 g of dense yellow, hard solid.

1.1.3 3-Propenyl 3-iodomethyl-7-phenylacetamido-5-thia-1-azabicyclo[4.2.0]oct-2-ene-2-carboxylate A. Preparation of cefaloram 3-propenyl ester A solution of sodium cefaloram (8.0 g) in 150 ml of water was cooled to 0° C. and then acidified to approximately pH 2 with 1N HCl. The solid which precipitated was filtered and dried under high vacuum to yield 5.9 g (78%) of the cephalosporin acid. This product (5.86 g, 15.0 mmole) was then suspended in 32 ml 5:3 DMF/dioxane solution, along with sodium bicarbonate (1.39 g, 16.5 mmole) and allyl iodide (2.05 ml, 22.5 mmole). The reaction mixture was stirred for 42 hours and then poured into a mixture of 400 ml ethyl acetate and 75 ml brine. The organic layer was extracted with 3×75 ml of brine, 75 ml of water, 3×75 ml of saturated NaHCO$_3$, and 75 ml of water and then dried over Na$_2$SO$_4$. Removal of solvents by rotary evaporation under high vacuum yielded 4.2 g crude product which was purified by flash chromatography on a 4.8×10 cm silica gel column with the following hexane/ethyl acetate elution gradient: (1) 3:1, 1L, (2) 1:1, 1L, and (3) 1:3, 1L. Appropriate fractions containing the product were combined, concentrated to dryness by rotary evaporation, and dried under high vacuum to yield the desired product (1.702 g, 26.4%).

Analysis Calcd. for C$_{21}$H$_{22}$N$_2$O$_6$S•0.5 H$_2$O: C, 57.39; H, 5.28; N, 6.37. Found: C, 57.48; H, 5.10; N, 6.25.

B. 3-Propenyl 3-iodomethyl-7-phenylacetamido-5-thia-1-azabicyclo[4.2.0]oct-2-ene-2-carboxylate A solution of trimethylsilyl iodide (0.800 ml, 5.6 mmole) and 3-propenyl cefaloram (1.20 g, 2.8 mmol) obtained in Step (a) was stirred in 30 ml of methylene chloride under nitrogen at room temperature for 1 hour. An additional 20 ml of methylene chloride was added, and then the reaction mixture was extracted with 30 ml of water, 2×50 ml of sodium metabisulfite, and 30 ml of water. The organic layer was dried over sodium sulfate, and solvents were removed by rotary evaporation and drying under high vacuum to provide the title compound (1.10 g, 79%).

$^1$H NMR (CDCl$_3$) δ: 7.4–7.1 (m, 5H), 6.1 (d, 1H), 6.1–5.8 (m, 1H), 5.8 (dd, 1H), 5.4–5.2 (m, 2H), 4.9 (d, 1H), 4.72 (d, 2H), 4.32 (q, 2H), 3.7 and 3.4 (q), 3.6 (d).

1.1.4 3-Propenyl 3-[[(2-hydroxy)ethyl]thio-methyl]-7-phenylacetamido-5-thia-1-azabicyclo-[4.2.0]oct-2-ene-2-carboxylate A solution of the 3-iodomethyl cephalosporin allyl ester from Preparation I above (1.10 g, 2.21 mmole), 2-mercaptoethanol (0.309 ml, 4.42 mmole), and 2,6-lutidine (0.386 ml, 3.32 mmole) was stirred for 1 hour at room temperature under N$_2$ in 30 ml of methylene chloride. After extracting with 4×50 ml 0.1N acetic acid, the organic layer was dried and concentrated by rotary evaporation. NMR analysis indicated that all starting material had not been consumed; therefore, the residue was redissolved in 30 ml of methylene chloride and retreated with mercaptoethanol (0.150 ml, 2.20 mmole) and 2,6-lutidine (0.190 ml, 3.30 mmole) under N$_2$ for 3 days. The reaction mixture was worked up as before. Flash chromatography was carried out on a 1"×3" silica gel column using an ascending gradient of ethyl acetate in hexane (25%–75% ethyl acetate). The product, which eluted at an ethyl acetate concentration of 35%–45%, was isolated by rotary evaporation and dried under high vacuum. The product weighed 175 mg (18%).

Analysis Calcd. for $C_{21}H_{24}N_2O_5S_2 \cdot 0.5\ H_2O$: C, 55.13; H, 5.51; N, 6.12. Found: C, 55.44; H, 5.28; N, 6.05.

FAB MS: MH$^+$ 449; MW observed 448.

$^1$H NMR (CDCl$_3$) δ: 7.3 (m, 5H), 6.1 (d, 1H), 5.85 (m, 1H), 5.73 (dd, 1H), 5.4–5.2 (m, 2H), 4.9 (d, 1H), 4.64 (d, 2H), 3.85 and 3.2 (q), 3.6 (d), 2.75–2.5 (m, 2H).

$^{13}$C NMR (CDCl$_3$): 171.0, 164.0, 134.0, 131.0, 129.9, 129.3, 129.1, 127.6, 119.5, 66.7, 61.2, 59.0, 57.9, 43.2, 33.9, 32.9, 27.4.

1.1.5 Diphenylmethyl 3-[[(2-hydroxy)ethyl]thio-methyl]-7-phenylacetamido-5-thia-1-azabicyclo [4.2.0]oct-2-ene-2-carboxylate Neat 2-mercaptoethanol (0.69 ml, 10.1 mmol) was added to a solution of diphenylmethyl 3-iodomethyl-7-phenylacetamido-5-thia-1-azabicyclo[4.2.0]oct-2-ene-2-carboxylate (6.0 g, 9.8 mmol) and 2,6-lutidine (1.14 ml, 9.9 mmol) in 50 ml of dry dimethylformamide stirring at 25° C. under N$_2$. The reaction was stirred for 52 hours and then poured into a separatory funnel containing 450 ml of 8:1 EtOAc/Et$_2$O and 450 ml of water. The reaction mixture was shaken and the water layer discarded. The organic extract was dried over anhydrous Na$_2$SO$_4$ and concentrated in vacuo. Flash chromatography over SiO$_2$ using 20% through 40% EtOAc/Hexane as eluent provided 1.85 g (32%) of the desired product as an off-white solid.

$^1$H NMR (CDCl$_3$) δ: 7.44–7.22 (m, 15H), 6.87 (s, 1H), 6.07 (d, J=9.2 Hz, 1H), 5.80 (dd, J=9.0, 4.9 Hz, 1H), 4.96 (d, J=4.8 Hz, 1H), 3.74 (d, J=4.8 Hz, 1H), 3.62 (m, 2H), 3.56 (m, 2H), 3.50 (d, J=4.9 Hz, 1H), 3.7–3.4 (m, 2H, partially obscured), 2.50 (m, 2H).

1.1.6 3-[[(2-hydroxy)ethyl]thiomethyl]-7-phenylacetamido-5-thia-1-azabicyclo[4.2.0]oct-2-ene-2-carboxylic acid Solid diphenylmethyl 3-[[(2-hydroxy)ethyl]thiomethyl]-7-phenylacetamido-5-thia-1-azabicyclo[4.2.0]oct-2-ene-2-carboxylate (1.21 g, 2.10 mmol) was suspended in 4 ml of anisole. Care was taken to ensure all of the solid was wetted with the solvent. The flask was cooled in an ice-water bath, and then 10 ml (0.13 mmol) of precooled trifluoroacetic acid (2° C.) was added via syringe. The reaction mixture was stirred for 5 minutes, and then the cooling bath was removed. The reaction was stirred for 30 minutes (room temperature, 25° C.), and then the volatiles were removed on high vacuum. Analysis by thin layer chromatography on silica gel showed 3 major products when visualized under U.V. after elution with 8:1:0.5 chloroform:isopropyl alcohol:acetic acid. Flash chromatography using 8:0.5:0.5 followed by 8:1:.5 and then 8:2:1 mixtures of the same solvents as eluents provided the 3 products. The most polar product was triturated with diethylether to provide 154 mg (18%) of the desired product as a white solid. The ether washes were collected and stored in a freezer after concentration to give an oil.

$^1$H NMR (DMSO-d$_6$) δ: 9.07 (d, J=8.4 Hz, 1H), 7.29–7.19 (m, 5H) 5.57 (m, 1H), 3.71–3.2 (m, 8H), 2.5–2.46 (m, 2H).

1.1.7 Diphenylmethyl 3-[(2-carboxyethyl)thiomethyl]-7-phenylacetamido-5-thia-1-azabicyclo[4.2.0]oct-2-ene-2-carboxylate Neat 3-mercaptopropionic acid (0.93 ml, 10.6 mmol) was added to a solution of diphenylmethyl 3-iodomethyl-7-phenylacetamido-5-thia-1-azabicyclo[4.2.0]oct-2-ene-2-carboxylate (3.244 g, 5.31 mmol) and 2,6-lutidine (1.86 ml, 15.93 mmol) stirring at 25° C. in 50 ml of dichloromethane under a nitrogen atmosphere. After stirring for 24 hours, the reaction mixture was poured into 0.5N HCl and extracted with 3 portions of CH$_2$Cl$_2$. The combined organic extracts were dried over Na$_2$SO$_4$, concentrated, and purified by flash chromatography over SiO$_2$ using a gradient of 40%–100% EtOAc/Hexane as eluent to provide the desired product as an off-white solid (1.28 g, 41%).

$^1$H NMR (CDCl$_3$) δ: 7.4–7.2 (m, 15H), 6.92 (s, 1H), 6.22 (d, J=10 Hz, 1H), 5.80 (dd, J=9.3, 4.8 Hz, 1H), 5.00 (d, J=5.9 Hz, 1H), 3.65 (m, 2H), 3.56 (ABQ, J=94.3, 14.0 Hz, 2H), 3.52 (m, 2H), 2.8–2.4 (m, 4H).

1.1.8 3-[(2-carboxyethyl)thiomethyl]-7-phenylacetamido-5-thia-1-azabicyclo[4.2.0]oct-2-ene-2-carboxylic acid Diphenylmethyl 3-[(2-carboxyethyl)thiomethyl]-7-phenylacetamido-5-thia-1-azabicyclo[4.2.0]oct-2-ene-2-carboxylate (1.01 g, 1.71 mmol) in a 50 ml round-bottom flask was wetted with 3 ml of anisole. The reaction flask was cooled in an ice-water bath and 10 ml (0.13 mmol) of trifluoroacetic acid (precooled to 2° C.) was added. After 5 minutes, the cooling bath was removed. The reaction mixture was stirred for 35 minutes at ambient temperature, and then the volatiles were removed by high vacuum. The remaining yellow solid was dissolved momentarily in 25 ml of dichloromethane, and then a white solid precipitated. Filtration by suction and drying under vacuum provided 402 mg (56%) of the desired diacid.

FAB MS (NOBA): 436.

$^{13}$C NMR (DMSO-d$_6$) δ: 172.8, 170.9, 164.5, 163.0, 135.8, 128.9, 128.2, 128.1, 126.4, 124.6, 58.8, 57.9, 41.5, 34.3, 32.3, 26.7, 25.6.

1.1.9 Diphenylmethyl 3-[[(4-nitrophenoxy)carbonyloxy]methyl]-7-phenylacetamido-5-thia-1-azabicyclo[4.2.0]oct-2-ene-2-carboxylate Pyridine (0.200 ml, 2.5 mmole) was added to a stirring suspension of diphenylmethyl 3-hydroxymethyl-7-phenylacetamido-5-thia-1-azabicyclo[4.2.0]oct-2-ene-2-carboxylate (1.030 g, 2.0 mmole) and p-nitrophenyl chloroformate (444 mg, 2.2 mmole) in 20 ml of methylene chloride under N$_2$ at room temperature. After stirring for 75 minutes, the solvent was removed by rotary evaporation. Flash chromatography was carried out on a 1×5 cm silica gel column with an ascending gradient of ethyl acetate in hexane (25%–50% ethyl acetate). On sitting, those fractions which contained the carbonate product produced crystals, which were filtered, combined, and washed with ethyl acetate/hexane (1:1). The product was dried under high vacuum. Yield of the product was 517 mg (38%).

M.P.: 161°–162.5° C.

Analysis Calcd. for $C_{36}H_{29}N_3O_9S$: C, 63.62; H, 4.30; N, 6.18. Found: C, 63.35; H, 4.10; N, 6.10.

FAB MS: MH$^+$ 680.

$^1$H NMR (CDCl$_3$) δ: 8.25 (d, 2H), 7.2–7.4 (m, 17H), 6.9 (s, 1H), 6.0 (d, 1H), 5.87 (dd, 1H), 5.2 and 4.95 (q, 2H), 4.95 (d, 1H), 3.6 (d, 2H), 3.5 (q, 2H).

1.1.10 Diphenylmethyl 7-phenylacetamido-3-[[(1,2,2,2-tetrachloroethoxy)carbonyloxy]methyl]-5-thia-1-azabicyclo[4.2.0]oct-2-ene-2-carboxylate Diphenylmethyl 3-hydroxymethyl-7-phenylacetamido-5-thia-1-azabicyclo[4.2.0]oct-2-ene-2-carboxylate (5.15 g, 0.010 mole) and 1,2,2,2-tetrachloroethyl-chloroformate (1.53 ml, 0.010 mole) were stirred and partially dissolved at 0° C. in 125 ml CH$_2$Cl$_2$ under N$_2$ Pyridine (0.97 ml, 0.012 mole) was then added slowly while maintaining temperature at 0° C. After the addition was complete, all material dissolved and the reaction mixture was warmed to room temperature with stirring for 30 minutes. The contents of the reaction vessel were transferred to a separatory funnel and the organic layer was extracted twice with 75 ml cold 0.5N HCl and once with 75 ml $H_2O$. The organic layer was separated and dried over $Na_2SO_4$. This was rotary evaporated to a foam, then dried under high vacuum at 35° C. to yield 7.15 g (99%) of the product.

$^1$H-NMR ($CDCl_3$): 7.4–72 (m, 15H), 6.90 (s, 1H), 6.60 (3, 1H), 5.97 (d, 1H), 5.87 (dd, 1H), 5.1 (m, 2H), 4.93 (d, 1H), 3.62 (dd, 2H), 3.45 (dd, 2H).

$^{13}$C-NMR ($CDCl_3$): 171.5, 165.3, 160.7, 151.8, 139.2, 139.1, 133.9, 129.7–127-6 (multiple peaks), 124.8, 124.7, 91.3, 80.3, 68.43, 68.37, 59.4, 57.7, 43.4, 26.4.

FAB MS: (NOBA+KI) $[M+K]^+$ at m/e 763.

Microanalysis: Calculated for $C_{32}H_{26}N_2O_7Cl_4S$: C, 53.05; H, 3.62; N, 3.87. Found: C, 52.97; H, 3.47; N, 3.80.

1.2 Preparation of Cephalosporin Cytotoxic Agent Prodrugs 1.2.1 3-[[[4-[Bis(2-chloroethyl)amino]-phenyl]aminocarbonyloxy]methyl]-8-oxo-7-(phenylacetamido)-5-thia-1-azabicyclo[4.2.0]oct-2-ene-2-carboxylic acid (hereinafter referred to as CM)

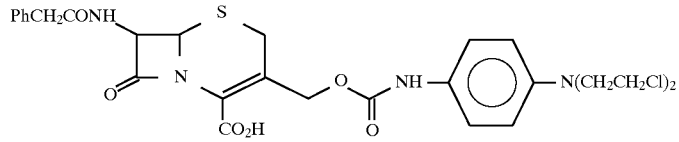

(XIV)

A solution of the crude isocyanate prepared above (3.92 g, 0.0151 mol) in 10 ml of dry DMF dimethylformamide was added to a solution of the cephalosporin potassium salt prepared above (2.65 g, 0.00688 mol) stirring at 25° C. under a nitrogen atmosphere. Immediately, triethylamine (2.7 ml, 0.020 mol) was added. The reaction was stirred for 26 hr and then poured into a mixture of 500 ml 1:1 EtOAc/water. After shaking, 100 ml diethyl ether was added to the emulsion. The organic layer was separated. The aqueous layer was acidified to pH 5 using 1N HCl and extracted with 200 ml diethyl ether. The organic extract was separated and the remaining aqueous layer was further acidified to pH 3. The organic layer which formed was separated. All three organic layers were dried separately over anhydrous $Na_2SO_4$ and concentrated separated in vacuo. Each fraction was flash chromatographed separately on Baker Octadecyl $C_{18}$ using 20% then 30% then 40% $CH_3CN$/water as eluent. Each pure fraction was concentrated separately on a rotary evaporator under vacuum at 30° C. until nearly all of the acetonitrile had been removed. The aqueous solutions were filtered through glass wool to remove the dark red oily solids which had precipitated. The water was removed on a freeze dryer and the remaining slightly yellowish, white fluffy solids were combined and dried for 12 hr in vacuo at 25° C. over $P_2O_5$. The slightly impure, overlap fractions from the chromatography and the previously removed red solids were combined and rechromatographed as above to provide additional product after drying in vacuo. The total yield of product was 280 mg (9%) of light yellowish, white colored fluffy solid. (IR [KBr] 3404 b, 3060, 2958, 1780, 1724, 1666, 1666, 1522, 1392, 658 $cm^{-1}$; FAB/NOBA $MH^+$ calcd for $C_{27}H_{29}N_4O_6Cl_2S$= 607.1185, found=607.1171; $^1$H NMR [DMSO- d6] δ 13.85–13.55 [bs, 1H], 9.41 [bs, 1H], 9.09 [d, J=8.2 Hz, 1H], 7.30–7.18 (m, 7H), 5.65 [m, 1 H], 5.07 [d, J=4.8 Hz, 1H], 5.01, 4.72 [2d, J=12.6 Hz, 2H], 3.66 [bs, 8H], 3.70–3.44 [m, 4H]; $^{13}$C NMR [DMSO-d6] 171.5, 165.2, 163.5, 153.9, 142.7, 136.3, 129.4, 128.6, 126.9, 120.6, 112.7, 63.1, 59.2, 57.6, 52.5, 41.6, 41.3, 25.7).

1.2.2 3-[[(N-adriamycinyl)carbonyloxy]methyl]-7-phenylacetamido-5-thia-1-azabicyclo[4.2.0]oct-2-ene-2-carboxylic acid (hereinafter referred to as ADR-ceph)

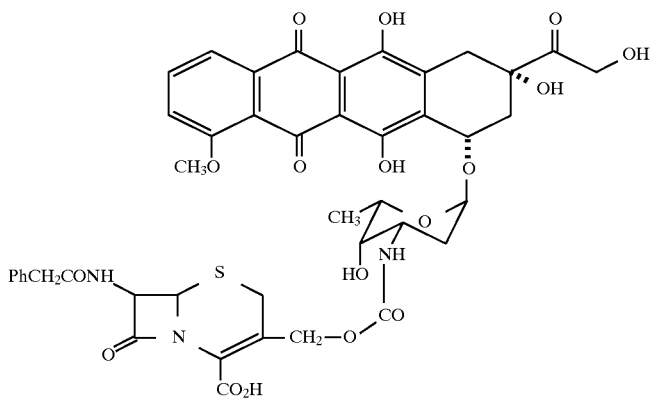

(A) Diphenylmethyl ester of ADR-ceph

Adriamycin hydrochloride (116 mg, 0.2 mmole), the cephalosporin p-nitrophenyl carbonate of Example 1.1.9

(122 mg, 0.18 mmole), and triethylamine (33 μl, 0.24 mmole) were stirred in 25 ml of DMF for 45 hours. Solvent was removed by rotary evaporation. The residue was redissolved in 100 ml ethyl acetate and extracted with 150 ml (0.1%) acetic acid. The aqueous layer was extracted with ethyl acetate, and the combined organic layers were concentrated to dryness by rotary evaporation. Flash chromatography was carried out on a 0.5"×6" silica gel column with $CH_2Cl_2$ followed by $CH_2Cl_2/CH_3OH$ (97:3). The red fractions were combined, concentrated, and rechromatographed as before (0.5"×3" column). Appropriate fractions containing the red component were combined, concentrated by rotary evaporation, and dried under high vacuum to yield 80 mg (41%) of the product.

FAB MS: $MH^+$ 1085; $M^+$ 1084.

$^1H$ NMR (selected peaks) δ: 7.9 (m), 7.7 (m), 7.1–7.4 (m), 5.7 (dd), 6.8 (s), 4.0 (d), 1.2 (d).

(B) Alternative procedure for the preparation of the diphenylmethyl ester of ADR-ceph The cephalosporin intermediate of Example 1.1.10 (72 mg, 0.10 mmole) was dissolved in 2 ml THF; this solution was then added dropwise to a stirring solution of Adriamycin hydrochloride (44 mg, 0.076 mmole) and $NaHCO_3$ (13 mg, 0.15 mmole) partially dissolved in 2 ml $H_2O$/1 ml THF at room temperature. After 1 hr., TLC and HPLC showed the reaction to be complete. The contents of the flask were diluted with 25 ml ethyl acetate and extracted once with 25 ml 0.1N HOAc. The organic layer was concentrated by rotary evaporation, then the residue was purified by flash chromatography on Merck silica gel 60 with the following series of eluants: (1) 200 ml $CH_2Cl_2$, (2) 100 ml $CH_2Cl_2$/EtOAc 9:1, (3) 100 ml $CH_2Cl_2$/EtOAc 8:2, (4) 100 ml $CH_2Cl_2$/MeOH 98:2, (5) 100 ml $CH_2Cl_2$/MeOH 96:4, and (6) 100 ml $CH_2Cl_2$/MeOH 92:8. The pure produce fraction was collected during the 2–4% MeOH elution. It was concentrated to dryness by rotary evaporation and further dried under high vacuum at 35° C. to yield 66 mg (80%) of the Adriamycin carbamate product.

$^1$H-NMR ($CDCl_3$): 13.95 (s, 1H), 13.18 (s, 1H), 7.99 (d, 1H), 7.75 (t, 1H), 7.36 (d, 1H), 7.3 (m, 15H), 6.81 (s, 1H), 667 (d, 1H), 5.76 (dd, 1H), 5.48 (s, 1H), 5.22 (m, 2H), 4.86 (d, 1H), 4.7 (m, 2H), 4.55 (s, 1H), 4.08 (m, 1H), 4.04 (s, 3H), 3.75 (q, 1H), 3.5 (broads, 3H), 3.3–2.85 (m, 4H), 2.58 (d, 1H), 2.34–2.12 (dd, 2H), 1.26 (d, 3H).

$^{13}$C-NMR ($CDCl_3$): 186.9, 186.5, 171.3, 165.2, 160.9, 160.6, 156.1, 155.5, 154.9, 139.0, 138.9, 135.7, 135.2, 133.7, 133.5, 130.4, 129.3–126.8 (multiple peaks), 124.8, 120.6, 119.7, 118.4, 111.4, 111.2, 100.6, 79.6, 69.5, 69.0, 67.2, 65.4, 62.8, 59.1, 57.6, 56.5, 47.1, 43.1, 35.5, 33.8, 29.8, 29.6, 26.0, 16.7.

FAB MS: $[M+K]^+$ at m/e 1123.

Microanalysis: Calculated for $C_{57}H_{53}N_3O_{17}S\cdot5.3H_2O$: C, 58.04; H, 5.43; N, 3.56. Found: C, 57.99;, H, 4.66; N, 3.60.

(C) Preparation of ADR-ceph

Trifluoroacetic acid (2.5 mL) was added rapidly to a stirred, cooled (ice/$H_2O$ bath) solution of diphenylmethyl ADR-ceph (1.0 g, 0.922 mmol) and anisole (2.5 mL) in methylene chloride (10 mL). Stirring was continued for 1.0 minute when the solution was poured into a stirred mixture of water containing ice. The pH was rapidly raised to 7.4 with the addition of less than one equivalent of dilute aqueous NaOH, followed by the addition of dilute aqueous $NaHCO_3$. The mixture was washed with ethyl acetate. The aqueous layer was filtered through diatomaceous earth. The filtrate was pumped onto a Michel-Miller HPLPLC column (22×300 mm) (purchased from ACE Glass. Column designed by K. H. Michel and R. F. Miller, U.S. Pat. No. 4,131,547) containing Partisil Prep 40 ODS-3 (Whatman Chemical Separation, Inc., Clifton, N.J.) which had been previously equilibrated with 0.02M ammonium phosphate (pH 6.5) buffer containing 10% acetonitrile. The column was eluted with 150 mL of this buffer and then was eluted with a solution of the buffer containing 40% acetonitrile whereupon the title compound rapidly eluted as a discrete red band. The product containing fractions were combined and were diluted with $H_2O$. The aqueous solution was layered with ethyl acetate and the pH was lowered to 3.4 with the addition of dilute HCl. The ethyl acetate layer was washed sequentially with $H_2O$, saturated NaCl and then was dried over $Na_2SO_4$. Removal of the ethyl acetate left the title compound (102 mg) as a bright orange solid. The pH of the combined aqueous washings was lowered to 2.5 with dilute HCl. Reextraction with ethyl acetate as previously described afforded an additional crop of the title compound (25 mg). Analytical HPLC showed each fraction to have the same area percent purity (>99).

HPLC: (retention time=8.14 minutes). Waters C18 radial pak cartridge. 2.0 mL/min of 60% pump A (0.05M, pH 6.5 ammonium phosphate plus 5% $CH_3CN$) and 40% pump B (80% $CH_3CN$-20% $H_2O$). Detect at 254 nm.

$^1$HNMR: (DMSO-$d_6$, 300 MHz) 6 13.99 (1H,s), 13.23 (1H,s), 9.05 (1H,d), 7.90–7.86 (2H,m), 7.60 (1H,dd), 7.27–7.19 (5H,m) 6.91 (1H,d), 5.60 (1H,dd), 5.42 (1H,S), 5.20 (1H,s), 5.01 (1H,d), 4.88 (3H,m), 4.73 (1H,m), 4.57 (3H,m), 4.14 (1H,m), 3.95 (3H,s), 3.67 (1H,m), 3.56–3.33 (6H,m), 2.96 (1H,d), 2.87 (1H,d), 2.18 (1H,d), 2.07 (1H,dd), 1.82 (1H,m), 1.45 (1H,m), 1.11 (3H,d).

$^{13}$C NMR: (DMSO-$d_6$, 360 MHz) δ 213.8, 186.6, 186.4, 170.9, 164.7, 162.8, 160.8, 156.1, 155.1, 154.5, 136.2, 135.8, 135.6, 134.7, 134.1, 129.0, 128.2, 126.4, 126.0, 124.5, 120.1, 119.8, 119.0, 110.8, 110.7, 100.3, 75.0, 69.9, 68.0, 66.7, 63.7, 62.5, 59.1, 57.4, 56.6, 47.2, 41.6, 36.7, 32.1, 29.8, 25.4, 17.0.

Mas Spectrum: (Positive ion FAB, NOBA+KI) m/z 956 $(M+K)^+$.

1.2.3 4-methoxybenzyl 7-phenylacetamido-3-[(N-t-BOC-melphananyl)methyl]-5-thia-1-azabicyclo[4.2.0]oct-2-ene-2-carboxylate

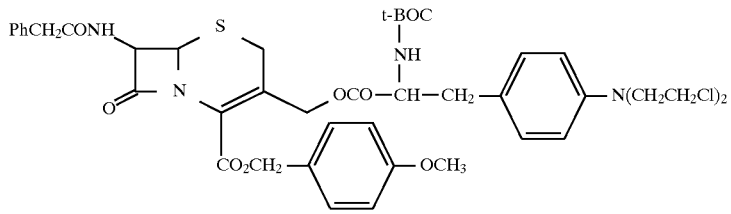

A suspension of 4-methoxybenzyl 3-chloromethyl-7-phenylacetamido-5-thia-1-azabicyclo[4.2.0]oct-2-ene-2-carboxylate (0.946 g, 2.0 mmole) and sodium iodide (1.20 g, 8.0 mmol) in 90 ml of acetone was stirred for 2 hours at room temperature. Solvent was removed by rotary evaporation. The residue was dissolved in 75 ml of methylene chloride and extracted with 3×50 ml (5%) of sodium metabisulfite and 50 ml of water. The product was dried over $Na_2SO_4$ and concentrated to dryness by rotary evaporation to provide the corresponding 3-iodomethyl cephalosporin ester (758 mg, 67%). This cephalosporin iodide (678 mg, 1.2 mmole) was then stirred in 25 ml of DMF with $NaHCO_3$ (101 mg, 1.2 mmole) and N-t-BOC-melphalan (486 mg, 1.2 mmole) for 3 hours at room temperature. After removal of solvent by rotary evaporation, the residue was dissolved in 75 ml of ethyl acetate and extracted with 3×50 ml of saturated $NaHCO_3$ and 50 ml of water. The organic layer was dried over $Na_2SO_4$, concentrated by rotary evaporation, and purified by 2 flash chromatographic procedures. In the first procedure, elution was carried out on a 2"×8" silica gel column with $CHCl_3/CH_3OH$ (97:3). In the second losporin ester. This cephalosporin iodide (610 mg, 1.0 mmole) was then stirred in 10 ml of DMF with $NaHCO_3$ (84 mg, 1.0 mmole) and N-t-BOC-melphalan (405 mg, 1.0 mmole) for 2 days at room temperature. After removal of solvent by rotary evaporation, the residue was dissolved in 100 ml of ethyl acetate and extracted with 3×75 ml of saturated $NaHCO_3$ and 50 ml of water. The organic layer was dried over $Na_2SO_4$, concentrated by rotary evaporation, and purified by flash chromatography on a 2"∴9" silica gel column with the following elution gradient: (1) $CHCl_3/CH_3OH$ (95:5, 600 ml), (2) $CHCl_3/CH_3OH$ (90:10, 400 ml), and (3) $CHCl_3/CH_3OH$ (80:20, 600 ml). Appropriate fractions were combined, and solvents were concentrated by rotary evaporation. Solid was isolated by trituration with hexane. It was filtered and dried under high vacuum. The yield of product was 117 mg (13%).

FAB MS: MW observed 900.

$^1$H NMR: 7.5–7.2 (m), 6.9 (d), 6.6 (d), 5.6 (dd), 5.2 (d), 3.7–3.5 (m), 3.15 (q), 1.4 (s).

1.2.5. 7-Phenylacetamido-3-($N^7$-mitomycin C)-5-thia-1-azabicyclo[4.2.0]oct-2-ene-2-carboxylic acid

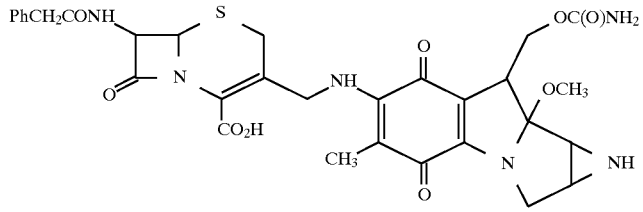

A solution of 3-azidomethyl-7-phenylacetamido-5-thia-1-azabicyclo[4.2.0]oct-2-ene-2-carboxylic acid (100 mg, prepared according to Cocker, J. D. et al, *J. Chem. Soc.,* 1965, 5015 at 5027–5028) in ethanol (10 mL) containing 70% $HClO_4$ (100 μL) was reduced at 35 psi over Pt (20 mg). After 18 h, silica gel TLC with n-BuOH:AcOH:$H_2O$ (4:1:1) as eluant indicated formation of a single more polar product that was positive by ninhydrin test for primary amine. Diisopropylethyl amine (175 μL) was added and volatiles were removed in vacuo. The residue was suspended in MeOH (10 mL) and was treated with diisopropylethyl amine (100 μL) and mitomycin A (70 mg). The dark mixture was stirred under nitrogen for 18 h. Silica gel TLC with the same solvent system as above indicated completion of the reaction with the formation of a compound more polar than mitomycin A. The dark reaction mixture was adsorbed on to C-18 procedure, the partially purified product was eluted on the same size silica gel column with $CHCl_3$ (500 ml) followed by $CHCl_3/CH_3OH$ (97:3, 400 ml). Appropriate fractions were combined, and solvents were partially concentrated by rotary evaporation. Solid was precipitated by the addition of an ether/hexane solution. The solid was filtered and dried under high vacuum. The yield of product was 200 mg (19.5%).

FAB MS: $MH^+$ 855; MW observed 854.

$^1$H NMR ($CDCl_3$) δ: 7.5–7.2 (m), 7.0 (d), 6.9 (d), 6.6 (d), 6.0 (t), 5.8 (dd), 5.2 (s), 4.9 (d), 4.32 (q), 3.8 (s), 3.8–3.4 (m), 1.4 (s).

1.2.4 Diphenylmethyl 7-phenylacetamido-3-[(N-t-BOC-melphananyl)methyl]-5-thia-1-azabicyclo[4.2.0]oct-2-ene-2-carboxylate A suspension of diphenylmethyl 3-chloromethyl-7-phenylacetamido-5-thia-1-azabicyclo[4.2.0]oct-2-ene-2-carboxylate (1.038 g, 2.0 mmole) and sodium iodide (1.20 g, 8.0 mmole) in 25 ml of acetone was stirred for 2 hours at room temperature. Solvent was removed by rotary evaporation. The residue was dissolved in 75 ml of ethyl acetate and extracted with 3×75 ml of brine. The product was dried over $Na_2SO_4$ and concentrated to dryness by rotary evaporation to provide the corresponding 3-iodomethyl cephasilica gel (2 g) and the dry powder was layered on a C-18 column (15 cm×2.5 cm) equilibrated with water and eluted with water (150 mL) and MeOH:$H_2O$ (3:7). Fractions containing cephalosporin derivative of mitomycin were combined and evaporated in vacuo to give the title compound as a blue solid (60 mg).

To a greyish blue solution of the title compound (0.3 mg) in PBS (1 mL) was added BCP II (*Bacillus cereus penicillinase,* 10 μL, protein concentration=4.1 mg/mL).

Immediately the color changed to blue. SiO$_2$ TLC with MeOH:CHCl$_3$ (1:9) and n-BuOH:AcOH:H$_2$O (vide supra) indicated complete conversion to mitomycin C.

1.2.6 3-[[[4-Bis(2-chloroethyl)amino]phenyl]aminocarboxyloxy]methyl]-7-glutaroylamino-8-oxo-5-thia-1-azabicyclo [4.2.0]oct-2-ene-2-carboxylic acid

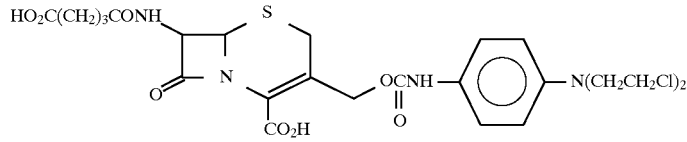

7-Glutaroylamino-3-hydroxymethyl-5-thia-1-azabicylo [4.2.0]oct-2-ene-2-carboxylic acid (disclosed in U.S. Pat. No. 3,912,589) is converted to the corresponding bistriethyl ammonium salt by dissolving the acid in 0.1M Et$_3$NHOAc (4 mL), and applying the solution to a column of C-18 (100 g, 24 cm×3 cm) equilbrated with the same buffer. The column is eluted with 0.1M Et$_3$NHOAc under nitrogen pressure, and fractions containing the desired salt are combined and evaporated in vacuo to give the bistriethylammonium salt of 7-glutaroylamino-3-hydroxymethyl-5-thia-1-azabicylo[4.2.0]oct-2-ene-2-carboxylic acid as a pale yellow gum after drying over P$_2$O$_5$ under vacuum. This material was used as is for subsequent coupling with isocyanate from phenylenediamine mustard.

To a magnetically stirred green suspension of phenylenediamine mustard hydrochloride (969 mg, 3.6 mmol) in absolute THF (40 mL) under N$_2$ at 0° C. was added diisopropylethyl amine (DIEA, 630 μL, 3.6 mmol). After 10 min, a solution of phosgene in toluene (1.9M, 1.95 mL) was added dropwise. After 1 h at 0° C., SiO$_2$ TLC with EtOAc:hexane (1:4) indicated completion of the reaction with the formation of the isocyanate as the major less polar product.

To a solution of the bistriethylammonium salt of 2 (1.64 g) in anhydrous DMF (10 mL) at 0° C. under N$_2$ was added DIEA (1.6 mL). After 5 min, the ice cold solution of the isocyante (vide supra) was canulated in a thin stream into the DMF solution. The orange solution was stirred at 0° C. for 3 h. The apparent pH of the reaction mixture was 5 and no more conversion took place by silica gel TLC (multiple developments with CHCl$_3$:MeOH:AcOH=89:10:1). The reaction mixture was diluted with acetonitrile (30 mL). Added 10 g of C-18 silica gel. Volatiles were removed in vacuo. The residue was applied to a C-18 column (12×2 cm) and eluted with 30%, 40%, and 50% acetonitrile in 1% acetic acid in water. Fractions containing the desired compound were combined and evaporated in vacuo to give a pale yellow gum (500 mg). Addition of EtOAc (6 mL) to this material resulted in the formation of a yellow solution from which the title compound crystallized out as a white fluffy solid (350 mg). High resolution MS: M$^+$=602.1022 (observed), 602.1005 (calculated).

$^1$H NMR (DMSO-d$_6$): 9.42 (s, 1H), 8.83 (d, 1H, NH, J=9 Hz), 7.26 (d, 2H, Ar-H, J=9 Hz), 6.68 (d, 2H, Ar-H, J=9 Hz), 5.66 (dd, 2H, 7-H, J=6 Hz and J=9 Hz), 5.10 (d, 1H, 6-H, J=6 Hz), 4.87 (dd, 2H, 3—CH$_2$O—, J=12 Hz), 3.67 (s, 8H, (NCH$_2$CH$_2$Cl)$_2$), 3.58 (dd, 2H, 2-H, J=18 Hz), 2.21 (m, 4H, 2' and 4'-H), 1.71 (m, 2H, 3'-H).

2. Biological Evaluation 2.1 Preparation of Materials 2.1.1 Purification and properties of B. cereus β-lactamase Commercially available E. coli and B. cereus β-lactamases were contaminated with other proteins, thus resulting in low specific activities. Analysis of the B. cereus δ-lactamase (Sigma Chemical Co.) by SDS-PAGE indicated the presence of a major band at 30 KD and a minor band at 25 KD. Partial separation of the two proteins was achieved by cation exchange chromatography.

Analysis of their activities using the cephalosporin-mustard as a substrate indicated that the minor constituent at 25 KD was responsible for the hydrolysis reaction. The proteins were separated in a manner similar that described by Davies, et al. Biochem J. 143:115–127, 1974, that involves first heat denaturation followed by chromatography on a Mono S cation exchange column (Pharmacia).

Figure 5:
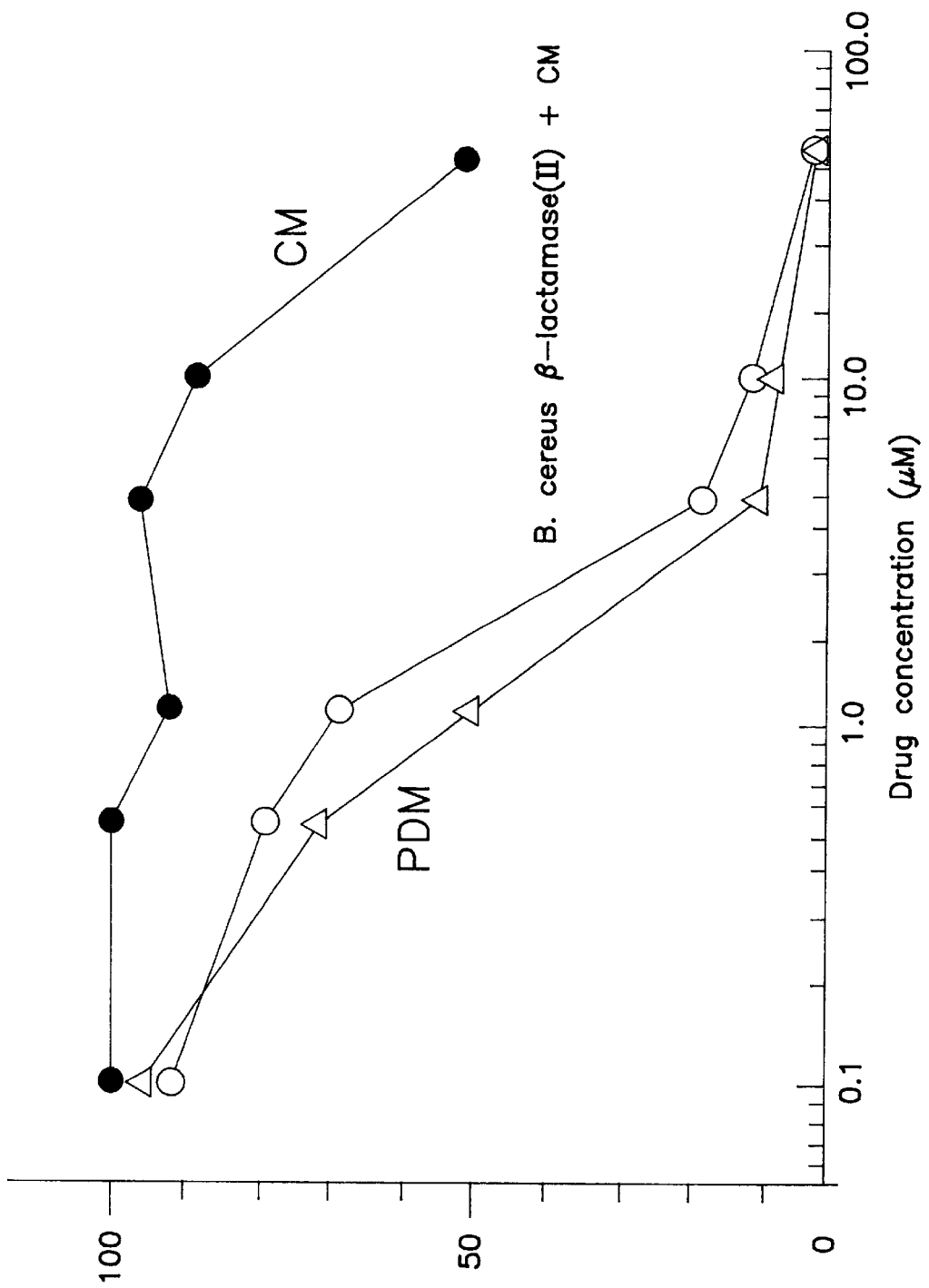
FIG. 5 shows the cytotoxicity of CM and PDM, administered alone, as compared to CM administered with purified *B. cereus* β-lactamase.

The 25 KD enzyme was highly purified as indicated by SDS-PAGE. EDTA (2.5 mM) completely inhibited the enzyme activity using CM as a substrate. These results are consistent with the classification of this enzyme as a B. cereus β-lactamase (II). See Bush, Antimicrobial Agents Chemother. 33:259, 1989. B. cereus β-lactamase hydrolyzed CM with a Km of 25 μM and a Vmax of 250 μmol min$^{-1}$mg$^{-1}$. At a concentration of 1.4 μg/ml, purified B. cereus β-lactamase (II) enhanced the cytotoxic activity of CM to the level observed for PDM (FIG. 5).

2.1.2 Conjugation of β-lactamase to Antibody

A solution of monoclonal antibody L6 (1–10 mg/ml) in phosphate buffered saline (PBS, pH 7.4) was adjusted to 0.015 mM in SMCC (Pierce Chemical Co., 3 mM in DMF). After 30 min the solution was applied to a G-25 Sephadex column and is eluted with 4× PBS.

B. cereus β-lactamase (Sigma Chemical Co.) at 4° C. in 10 mM phosphate/200 mM NaCl, pH 7.5 (1–10 mg/ml) was treated with iminothiolane (Pierce Chemical Co., 16.5 mM in 0.5M sodium borate, pH 8.5) so that the final iminothiolane concentration was 1.5 mM. The reaction was allowed to proceed at 4° C. for 90 min, and the protein was purified as above.

The two chemically modified proteins were allowed to react in a 1:1 molar ratio at 23° C. for 1 hr. The reactive groups were blocked by adding 2-aminoethanethiol (0.01–1 mM final concentration) followed 10 min later by N-ethylmaleimide or iodoacetamide (0.01–1.1 mM final concentration). The conjugates were purified in a two stage procedure involving size exclusion chromatography on an S-300 Sephacryl column (Pharmacia; PBS as eluant) and then ion exchange chromatography on a Mono S cation exchange column (Pharmacia; applied in PBS, eluted with high salt). The yield of conjugate (1:1 Mab/β-lactamase ratio) in this procedure ranged from 15–30%.

Figure 3:
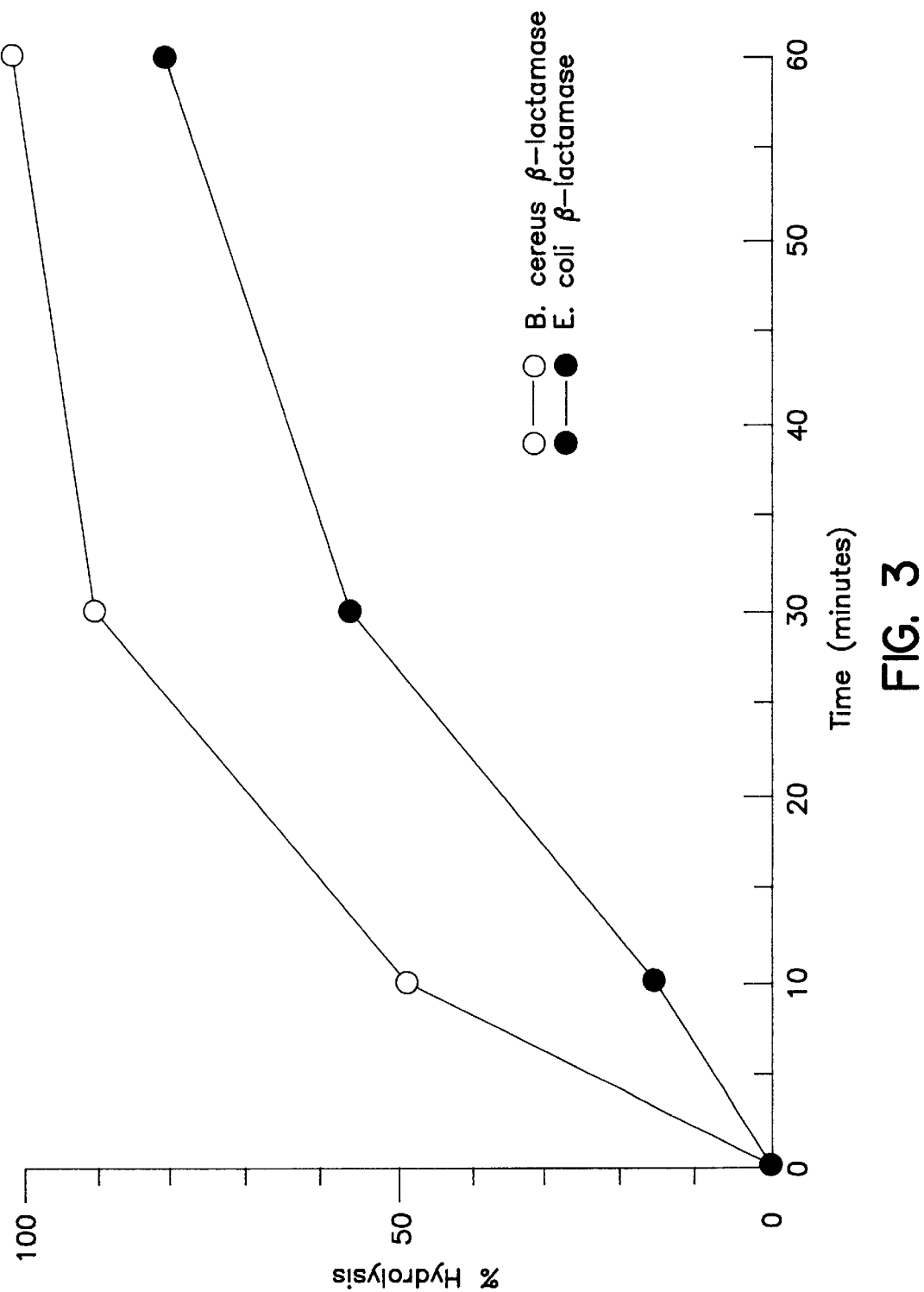
FIG. 3 shows kinetics of hydrolysis of CM catalyzed by crude samples of *E. coli* and *B. cereus* β-lactamases.

2.2 Enzymatic hydrolysis of cephalosporin-cytotoxic prodrug 2.2.1 Hydrolysis of CM by β-Lactamase Several commercially available β-lactamases were screened for activity using the cephalosporin mustard derivative, CM. The ability of these derivatives to hydrolyze CM was monitored by HPLC or by UV/vis spectrophotometric analysis. Partially purified samples of B. cereus β-lactamase (Sigma Chem. Co.) and E. coli β-lactamase (Boeringer Mannheim Biochemicals) were able to hydrolyze CM to release the nitrogen mustard, PDM. (FIG. 3)

To solutions of CM (50 μM) in PBS at 37° C. was added the commercially available samples of B. cereus or E. coli β-lactamase (3 μg total protein/ml). Aliquots (100 μl) were quenched by addition to methanol (100 μl) at 4° C., and precipitated proteins were removed by centrifugation. The samples (100 μl) were analyzed by HPLC using an IBM reverse phase C-18 column (4.6×250 mm) and the following gradient conditions: 50–100% buffer A to buffer B (buffer A is 0.08% aqueous diethylamine buffered to pH 2.3 with phosphoric acid; buffer B is 90% acetonitrile, 10% buffer A) over 15 min at 1 ml/min. Fractions were monitored at 266 nm.

2.2.2 Hydrolysis of ADR-ceph by β-Lactamase and L6-β-Lactamase Conjugate

The ability of the purified β-lactamase from B. cereus and the lactamase-L6 conjugate to catalyze the release of adriamycin from ADR-ceph was evaluated in human plasma at 37° C.

Stock solutions of the β-lactamase and lactamase-L6 conjugate were prepared in 0.05M Hepes buffer (pH 7). Aliquots of these stock solutions were added to solutions of ADR-ceph in human plasma thermostated at 37° C. The final concentration of ADR-ceph was 572 μg/ml in the β-lactamase experiment and 896 μg/ml in the L6-lactamase experiment; and the final concentrations of β-lactamase and L6-lactamase conjugate were 0.45 μg/ml and 5.4 μg/ml, respectively. Aliquots were withdrawn periodically and were added to two volumes of cold methanol (4° C.). The precipitated proteins were removed by centrifugation. The supernatants were analyzed by HPLC using a Waters Associates C$_{18}$ Radial Pak cartridge (8×100 mm). The column was eluted at 2.0 mL/min with a mobile phase of 60% of 0.05M ammonium phosphate (pH 6.5) containing 5% acetonitrile and 40% of a mixture of acetonitrile-water (80:20). The peaks were detected by uv at 254 nm. In these assays the respective retention times for adriamycin and ADR-ceph were 3.8 and 7.5 minutes.

Figure 7:
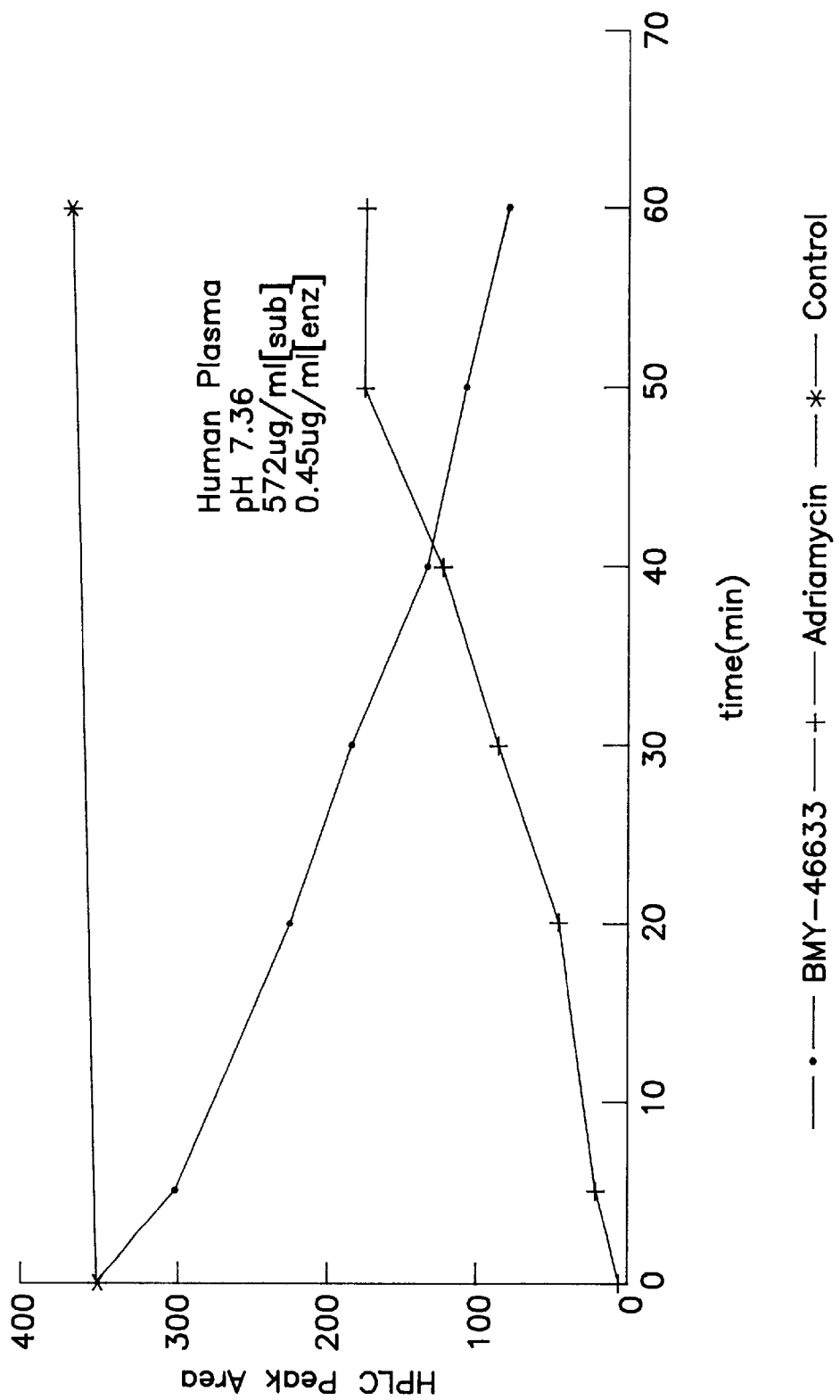
FIG. 7 depicts the release of adriamycin when ADR-ceph was treated with *B. cereus* β-lactamase in human plasma at 37° C.
Figure 8:
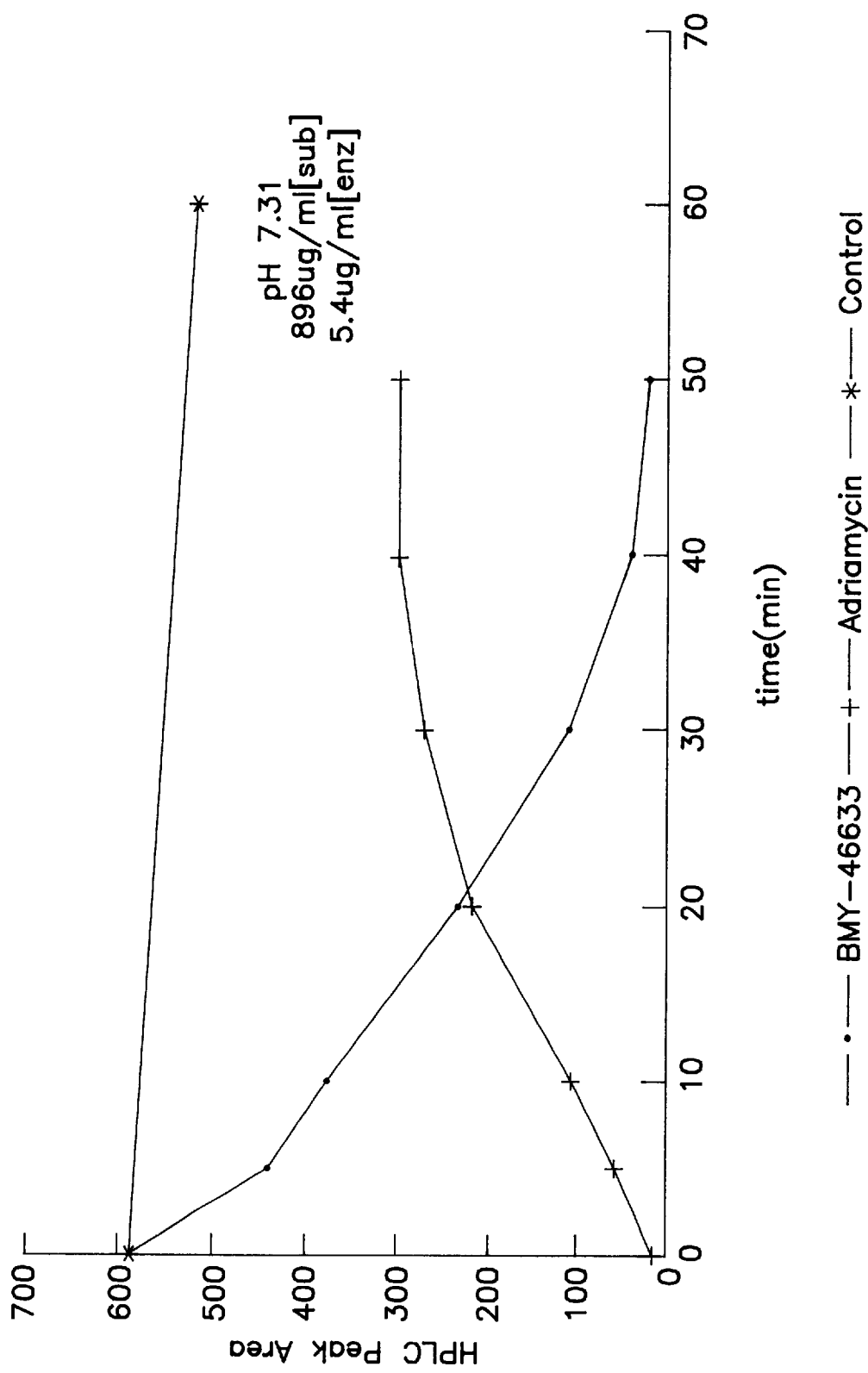
FIG. 8 shows the release of adriamycin when ADR-ceph was treated with L6-lactamase (from *B. cereus*) conjugate in human plasma at 37° C.

FIG. 7 shows the HPLC peak areas of ADR-ceph and adriamycin plotted against time when ADR-ceph was exposed to β-lactamase, and it demonstrates that ADR-ceph is efficiently hydrolyzed with B. cereus β-lactamase resulting in the rapid release of adriamycin. Similarly, FIG. 8 shows that the lactamase-L6 conjugate also efficiently releases adriamycin from ADR-ceph with a half life of 15 minutes at the concentrations of prodrug and enzymes utilized.

The specific activities of selected β-lactamases for ADR-ceph were examined. These enzymes were B. cereus β-lactamase, lactamase-L6 conjugate, Sigma penicillinase from E. cloacae (Sigma Chemical) and P99 cephalosporinase from E. cloacae. All enzymes were diluted to give protein concentrations of 0.20±0.01 mg/ml (with respect to β-lactamase). Assays were performed spectrophotometrically to 0.05M phosphate buffer, pH 7.0, at 25° C. Cephaloridine was used as a reference substrate for the enzymes.

The results of these experiments are provided in Table 1. P99 cephalosporinase had the highest specific activity for both cephaloridine and ADR-ceph. The L6-lactamase conjugate was slightly more active than the B. cereus β-lactamase alone, perhaps because the latter enzyme had to be diluted for assay purposes, thereby entertaining the possibility for loss of activity in dilute solution. The Sigma "penicillinase" had the lowest activity of all the preparations. This enzyme had the same isoelectric point as the P99 enzyme, suggesting that the two enzymes are the same. The differences in activity is probably due to differences in purity between the two preparations.

Kinetic parameters were determined for the L6-lactamase conjugate and the P99 cephalosporinase, and are given in Table II. Vmax was 3.5 times higher for the P99 enzyme. However, because the P99 enzyme had a higher Km value, the hydrolysis efficiency (Vmas/Km) of the two enzymes differed only two-fold. The two enzymes, therefore, are very similar in their hydrolytic properties.

TABLE 1

Hydrolysis of cephalosporin substrates by β-lactamases.

| Enzyme | Substrate (100 μg/ml) | μmoles/min/μg protein |
|---|---|---|
| B. cereus β-lactamase | Cephaloridine | 0.038 |
|  | ADR-ceph | 0.016 |
| L6-lactamase (B. cereus) conjugate | Cephaloridine | 0.045 |
|  | ADR-ceph | 0.021 |
| Sigma penicillinase from E. cloacae | Cephaloridine | 0.026 |
|  | ADR-ceph | 0.0030 |
| P99 cephalosporinase from E. cloacae | Cephaloridine | 0.30 |
|  | ADR-ceph | 0.060 |

TABLE 2

Hydrolysis parameters for ADR-ceph

| Enzyme | Km (μm) | Vmax μmoles/min/ug protein | Vmax/Km μmoles/min/μg pro/mM S |
|---|---|---|---|
| L6-lactamase (B. cereus) conjugate | 120 | 0.047 | 0.40 |
| P99 | 200 | 0.164 | 0.82 |

2.3 Additional Biological Evaluations 2.3.1 In vitro cytotoxicity of CM with β-lactamase The cytotoxic effects of CM and PDM were monitored using a human lung adenocarcinoma cell line, H2981. The cells were plated (in Iscove's modified Dulbecco's medium with 15% fetal calf serum [IMDM]) into 96 well microtiter plates at 8000 cells/well in 100 μl IMDM and allowed to adhere overnight at 37° C. The enzymes in 50 μl IMDM followed by the drugs PDM or CM in 50 μl IMDM were added to the wells so that the final enzyme concentration was 3 μg crude enzyme/ml or 1.4 μg pure enzyme/ml. After one hr, the cells were washed 3 times with IMDM, 200 μl of IMDM was added to each well, and the incubation was continued 17 hr at 37° C. The medium was removed and 200 μl of IMDM containing [$^3$H] thymidine (1 μCi/well) was added, and after 6 hr the cells were frozen to −70° C., thawed, and harvested onto glass fiber discs. The cytotoxic effects were determined by measuring the amount of $^3$H-thymidine incorporated into DNA versus an untreated control.

Figure 4A:
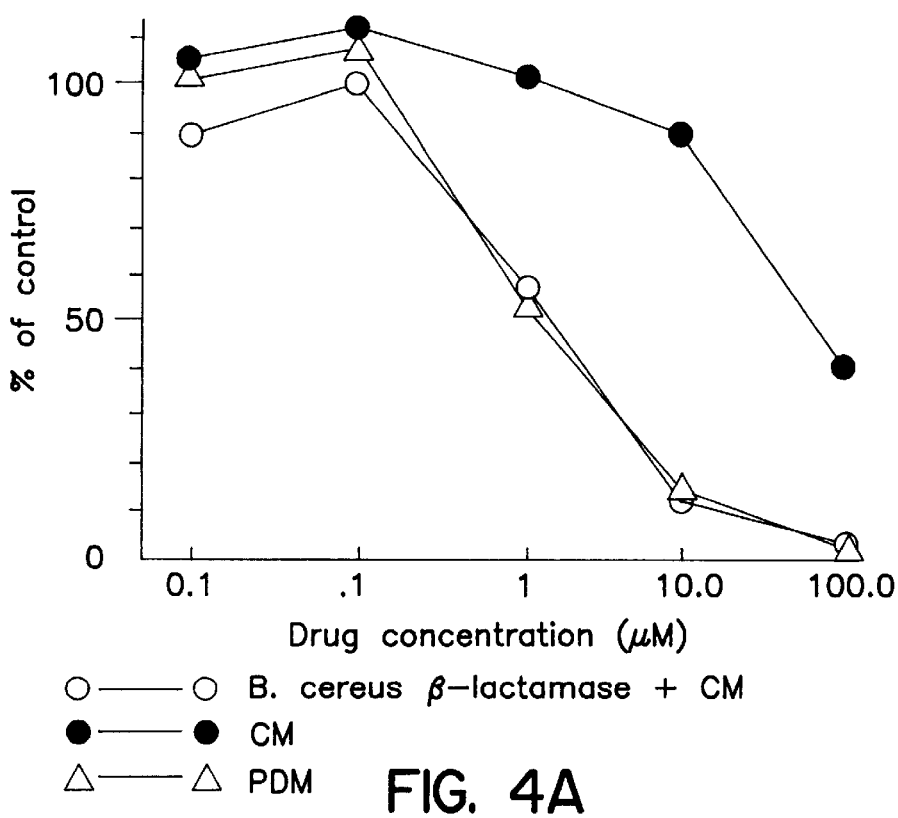
FIG. 4 depicts the cytotoxicity of CM and PDM, administered alone, as compared to CM administered with unpurified *E. coli* β-lactamases. In 4(A), *B. cereus* β-lactamase is used whereas the experiment depicted in 4(B) utilizes *E. coli* β-lactamase.
Figure 4B:
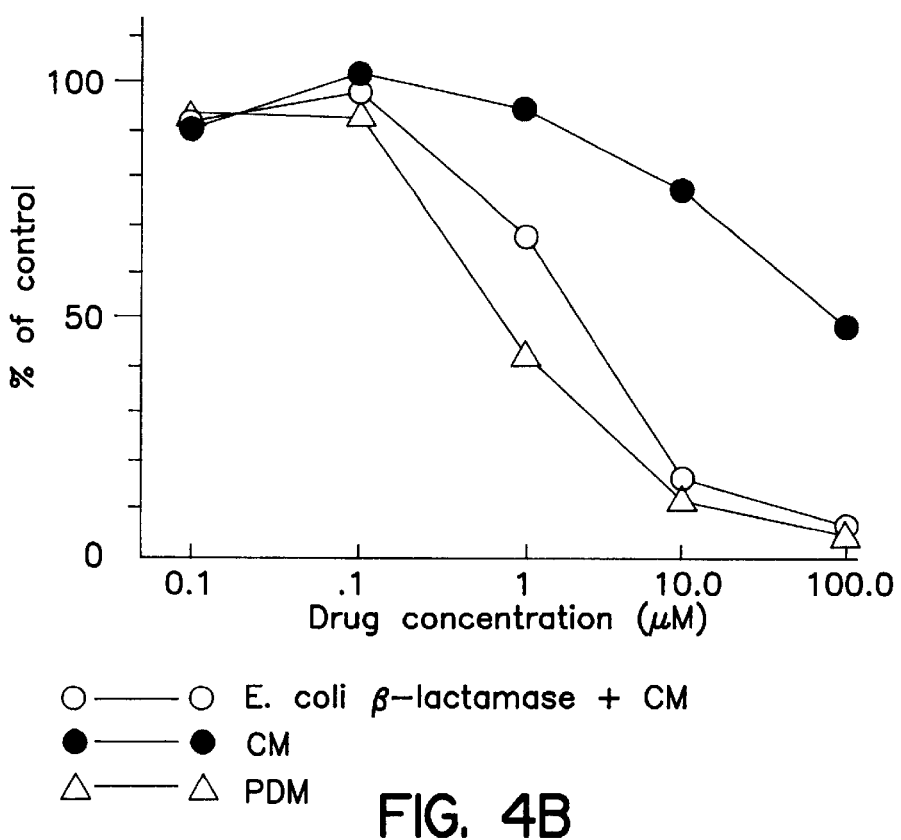

CM (IC$_{50}$ approximately 100 μM) was much less cytotoxic than PDM (IC$_{50}$ approximately 1 μM) (FIG. 4). The β-lactamases from B. cereus and from E. coli enhanced the activity of CM 50–100 fold. This is most likely due to the hydrolysis of CM by the enzymes, and the subsequent release of PDM.

2.3.2 In vitro cytotoxicity of CM with L6-β-lactamase conjugate

Figure 6:
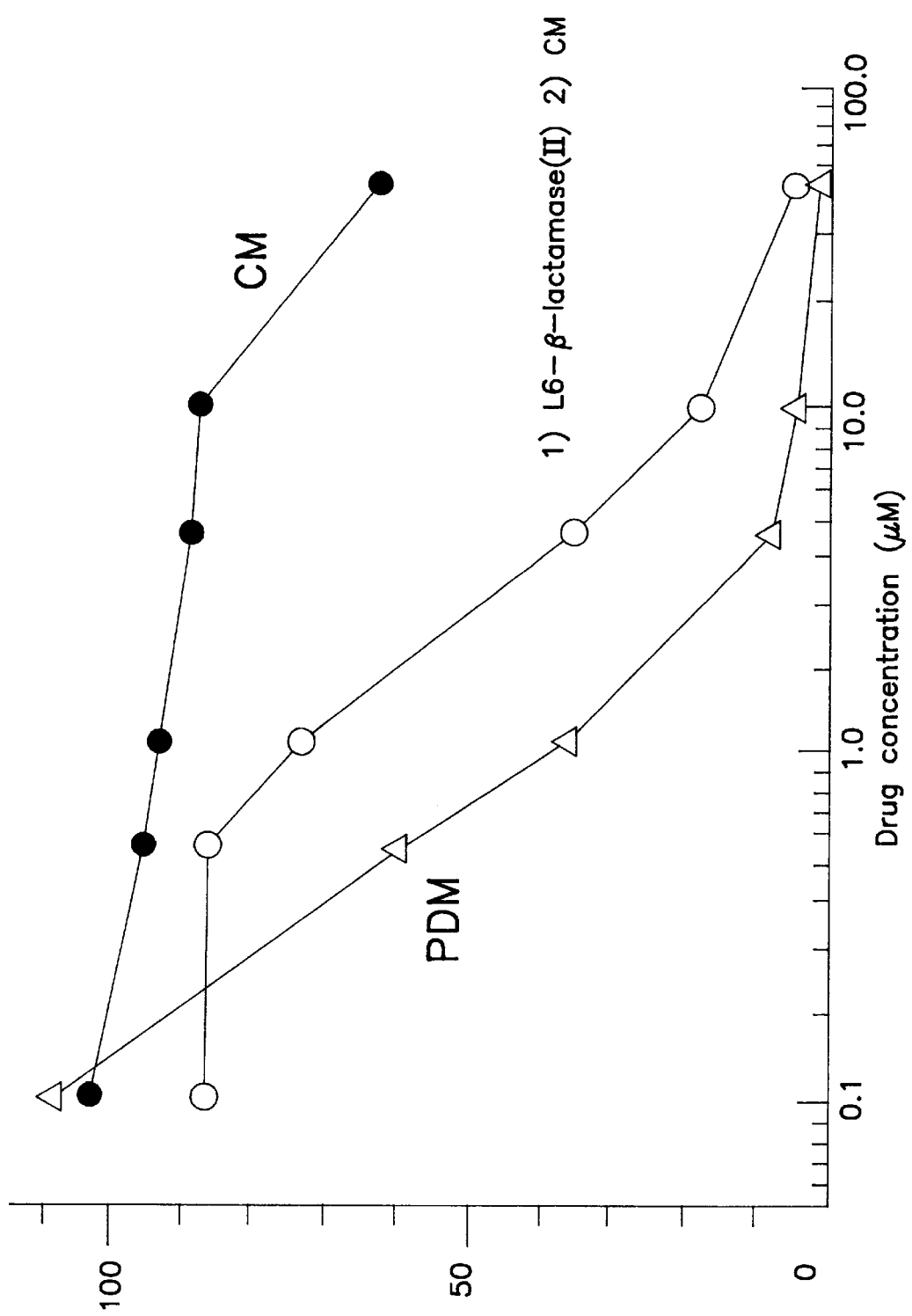
FIG. 6 shows the results of an in vitro cytotoxicity assay using an L6-β-lactamase conjugate delivered with CM.

The cytotoxic effects of CM administered with the antibody-β-lactamase conjugate were monitored as described above for CM and PDM in Example 2.3.1. H2981 lung cells were prepared as described above, then exposed to the L6-β-lactamase conjugate for 1 hr at 37° C. in IMDM containing 15% fetal bovine serum, washed twice, and then treated with CM as described in Example 2.3.1 above. Cells treated with CM or PDM as described in Example 2.3.1 were used as controls. The data, shown in FIG. 6, demonstrate the enhanced cytotoxic effect of administering the CM with the antibody-β-lactamase conjugate.

2.3.3 In vivo stability and toxicity of CM

The stability of CM and PDM in mouse plasma at 37° C. was determined by HPLC quantification of their consumption. PDM or CM (0.5 mM) in mouse plasma or IMDM cell growth medium was incubated at 37° C., quenched, and analyzed by HPLC as described above. PDM ($t_{1/2}$=20 min) was significantly more reactive in mouse plasma than CM (12% reaction after 150 min). A 10-fold difference in stability was observed in the media used for tissue culture ($t_{1/2}$for PDM and CM, 3 and 30 minutes respectively).

The toxic effects of PDM and CM were determined in Balb C nu/nu mice. The drugs were administered i.v. in doses spaced 24 hr apart, and the treatment was repeated after 1 week. Under these conditions, PDM was toxic at 50 μg/injection, and the maximum tolerated was approximately 38 μg/injection. No toxicity was observed for CM for doses as high as 900 μg/injection. On a molar basis this represented greater than an 11-fold difference in toxicity.

2.3.4 Stability of ADR-ceph

Figure 9:
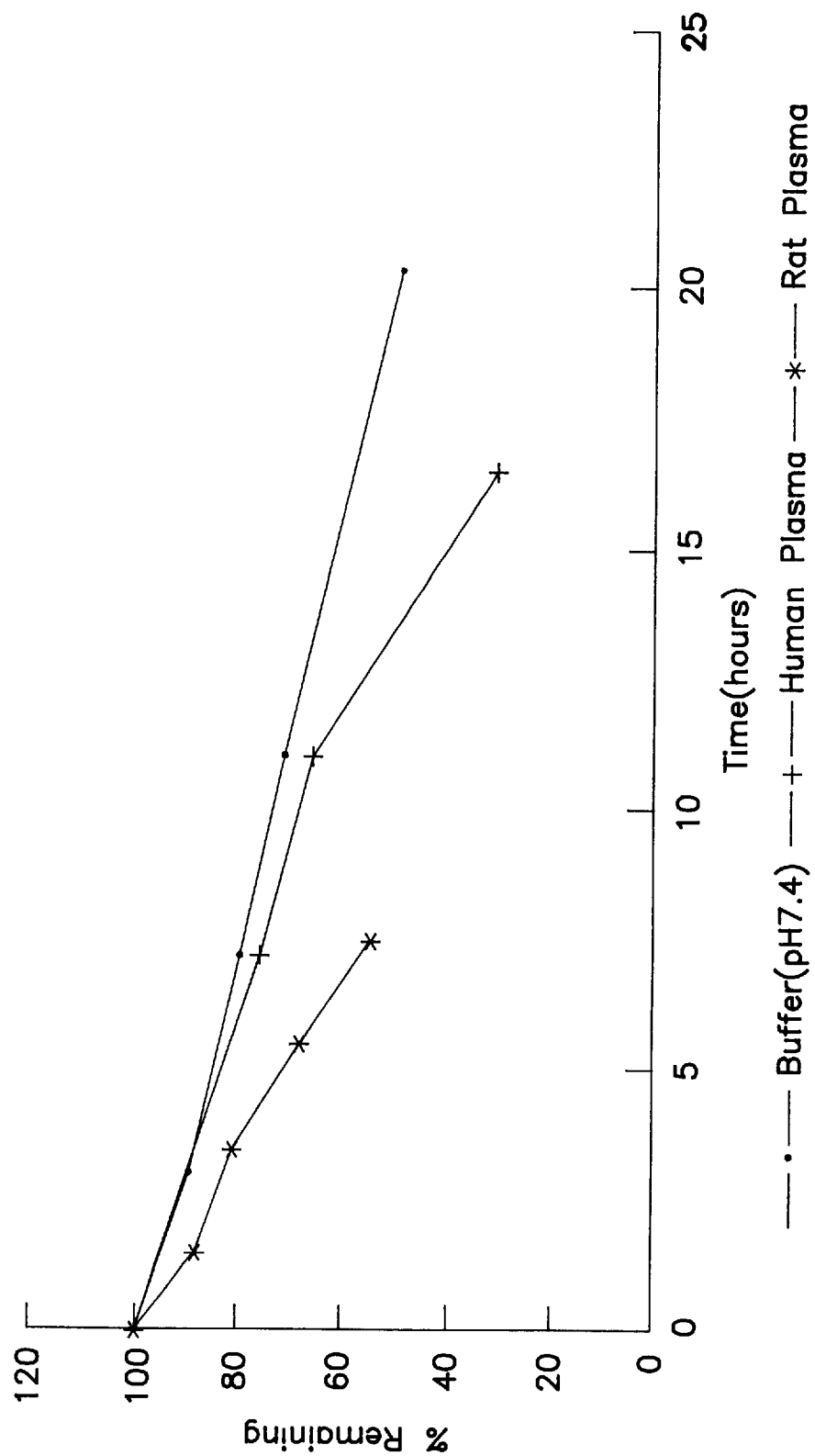
FIG. 9 shows the comparative stability of ADR-ceph at selected media at 37° C.

Using the same HPLC assay described in Example 2.2.2 the respective half lives at 37° C. of ADR-ceph in rat plasma, buffer at pH 7.4, and human plasma are 8, 20 and ≧12 hours (FIG. 9).

Thus, novel cephalosporin prodrugs and methods for their use have been disclosed. Although the preferred embodiments of the subject invention have been described in some detail, it is understood that obvious variations can be made without departing from the spirit and the scope of the invention as defined by the appended claims.

We claim:

1. A cephalosporin prodrug having the formula

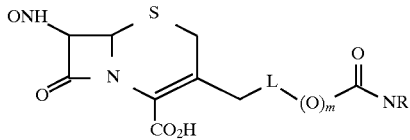

wherein

Q is hydrogen, an amine protecting group selected from the group consisting of a lower alkonyl, substituted lower alkonyl; aroyl, substituted aroyl; aralkyl, substituted aralkyl, aralkylidene, substituted aralkylidine; halogenated alkyl; alkoxycarbonyl substituted alkoxycarbonyl; aralkoxyfarbonyl substituted aralkoxycarbony; an unsubstituted substituted trialkylsilyloxycarbonyl triarylsilyloxycarbonyl; trialkylsilyl and triarylsilyl groups, or R—C(O)—, wherein R is (a) 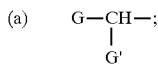

wherein G is a substituted or unsubstituted aryl, heterocyclic, cyclohexadienyl group; the substituents for the groups are 1 to 3 of the same or different groups selected from halogen, hydroxy, amino, alkoxy, alkylamino, dialkylamino, alkanoyloxy, carboxy. nitro, cyano, and alkoxycarbonyl; G' is hydrogen, hydroxy, amino, monoalkylamino, dialkylamino, alkanoylamino, alkanoyloxy, carboxy, or sulfo;

(b) 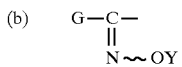

wherein G is as defined above, and Y is hydrogen, $C_{1-6}$ alkyl, or $C_{1-6}$alkanoyl;

(c) 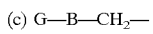

wherein G is as defined above, B is oxygen or sulfur; and (d) 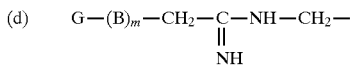

where G, and B are as defined above, and m is 0 or 1;

L is a direct bond or —S—$(CH_2)_n$—;

R is a compound having one functional group selected from amino, carboxyl, and hydroxyl groups, that is cytotoxic when released from said cephalosporin-prodrug;

n is 2, 3, or 4; and m is 0 or 1 with the proviso that, when L is a direct bond, m is 1; or a pharmaceutically acceptable salt thereof.

2. A cephalosporin prodrug of claim 1 having the formula:

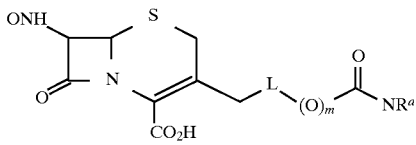

wherein $NR^a$ is a nitrogen containing cytotoxic agent; or a pharmaceutically acceptable salt thereof.

3. The cephalosporin prodrug of claim 1, wherein R is selected from the group consisting of etoposide, teniposide, adriamycin, daunomycin, carminomycin, aminopterin, dactinomycin, mitomycin, cis-platinum and cis-platinum analogues, bleomycins, esperamicins, and 5-fluorouracil.

4. The cephalosporin prodrug of claim 2, wherein $NR^a$ is a nitrogen mustard.

5. The cephalosporin prodrug of claim 2, wherein $NR^a$ is mitomycin C.

6. The cephalosporin prodrug of claim 2, wherein $NR^a$ is adriamycin.

7. The cephalosporin prodrug of claim 2 having the formula:

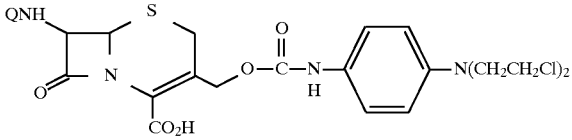

or a pharmaceutically acceptable salt thereof.

8. The cephalosporin prodrug of claim 7 wherein Q is glutaroyl.

9. The cephalosporin prodrug of claim 8 wherein Q is phenylacetyl or thienylacetyl.

10. The cephalosporin prodrug of claim 2 having the formula:

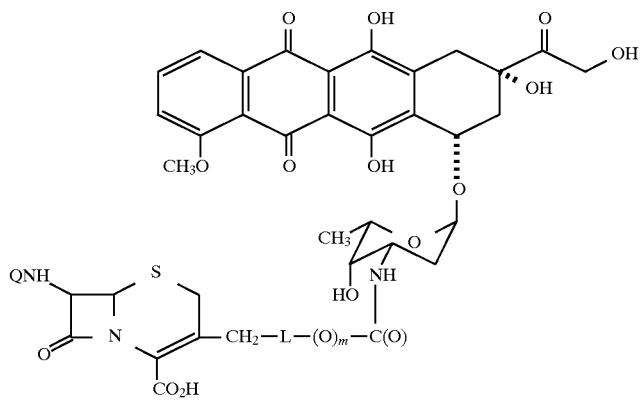

or a pharmaceutically acceptable salt thereof.

11. The cephalosporin prodrug of claim 10 having the formula:

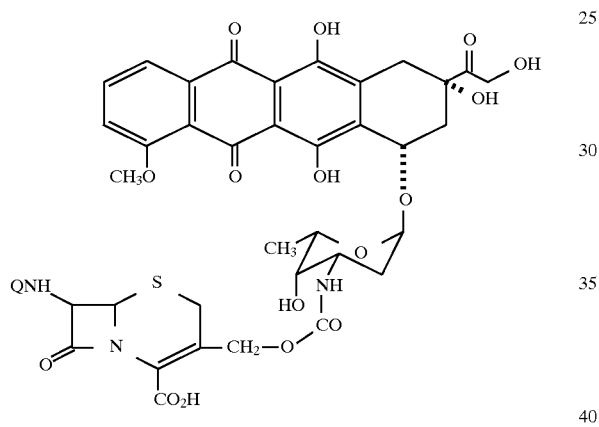

or a pharmaceutically acceptable salt thereof.

12. The cephalosporin prodrug of claim 11 wherein Q is phenylacetyl or thienylacetyl.

13. The cephalosporin prodrug of claim 12 wherein Q is phenylacetyl.

14. The cephalosporin prodrug of claim 2 having the formula:

15. The cephalosporin prodrug of claim 14 wherein Q is phenylacetyl or thienylacetyl.

16. The cephalosporin prodrug of claim 2 having the formula:

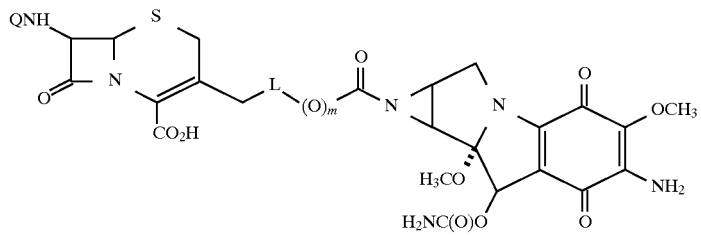

or a pharmaceutically acceptable salt thereof.

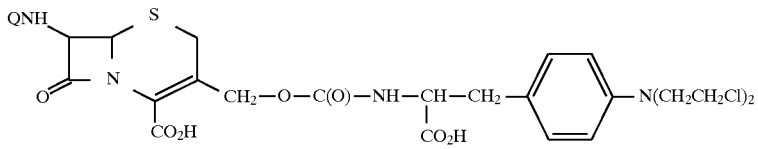

or a pharmaceutically acceptable salt thereof.

17. The cephalosporin prodrug of claim 16 wherein Q is phenylacetyl or thienylacetyl.

18. The cephalosporin prodrug of claim 2 having the formula:

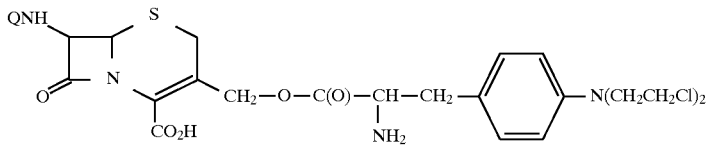

or a pharmaceutically acceptable salt thereof.

19. The cephalosporin prodrug of claim 18 wherein Q is phenylacetyl or thienylacetyl.

20. A cephalosporin prodrug having the formula:

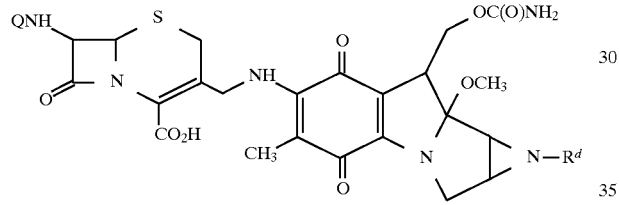

wherein $R^d$ is hydrogen or $C_{1-3}$ alkyl or a pharmaceutically acceptable salt thereof.

21. The cephalosporin prodrug of claim 20 wherein $R^d$ is hydrogen and Q is phenylacetyl or thienylacetyl.

22. A method for treating mammalian tumors comprising the step of administering to a mammal in need of such treatment a pharmaceutically effective amount of at least one antibody-β-lactamase conjugate and a pharmaceutically effective amount of at least one prodrug according to claim 1 or claim 20.

23. A method of claim 22 wherein said prodrug is selected from a prodrug of claims 8, 11, 16, 18 and 20.

24. A method for the delivery of a cytotoxic agent to tumor cells comprising:
 administering a pharmaceutically effective amount of at least one antibody-β-lactamase conjugate wherein said antibody is reactive with an antigen on the surface of said tumor cells; and
 administering a pharmaceutically effective amount of a cephalosporin prodrug of claim 1 or claim 20,
 whereby said cytotoxic agent is delivered to said tumor cell.

25. The method of claim 24, wherein said antibody is selected from the group consisting of polyclonal, monoclonal, or chimeric antibodies.

26. The method of claim 24, wherein said cytotoxic agent is selected from the group consisting of the adriamycin, mitomycin C, and nitrogen mustards.

27. The method of claim 24, wherein said cephalosporin prodrug has the formula:

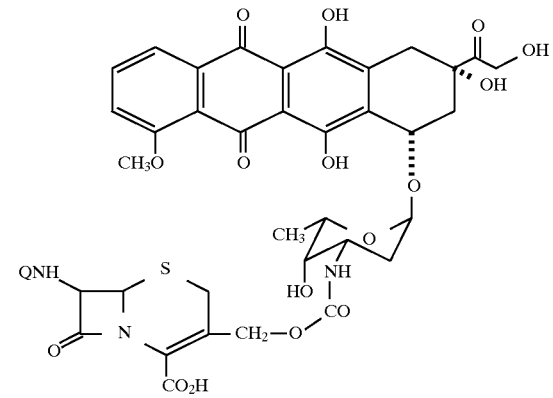

or a pharmaceutically acceptable salt thereof.

28. The method of claim 27, wherein Q is phenylacetyl or thienylacetyl.

29. The method of claim 24, wherein said cephalosporin prodrug is

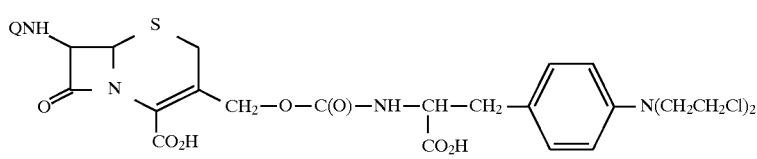

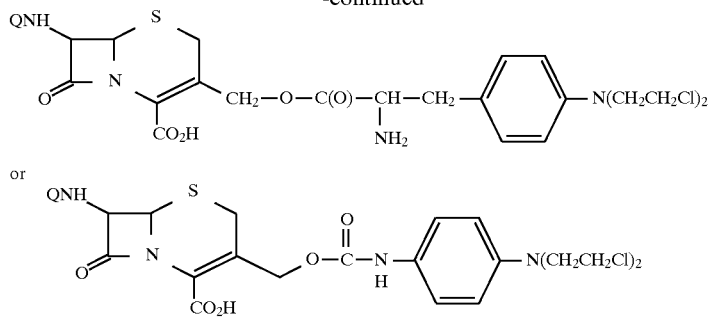

or a pharmaceutically acceptable salt thereof.

30. The method of claim 24 wherein said cephalosporin prodrug has the formula:

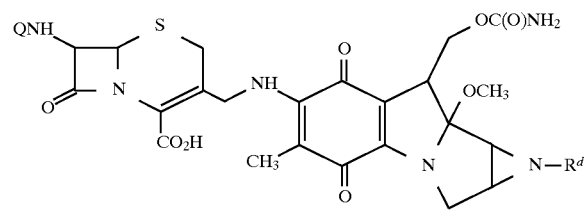

wherein $R^d$ is hydrogen or $C_{1-3}$ alkyl or a pharmaceutically acceptable salt thereof.

31. A method for the delivery of a cytotoxic agent to tumor cells comprising:
  administering a pharmaceutically effective amount of at least one fusion protein comprising at least the antigen binding region of an antibody reactive with a tumor-associated antigen linked to at least a functionally active part of β-lactamase; and
  administering a pharmaceutically effective amount of a cephalosporin prodrug.

32. The cephalosporin prodrug of claim 1 wherein Q is selected from the group consisting of: hydrogen, phenylacetyl, 2-thienylacetyl, α-hydroxyphenylacetyl, phenylglycyl, p-hydroxyphenylglycyl and (2-amino-4-thiazolyl)(methoxyimino)acetyl.

33. The method of claim 22 wherein the prodrug is one in which Q is selected from the group consisting of: hydrogen, phenylacetyl, 2-thienylacetyl, α-hydroxyphenylacetyl, phenylglycyl, p-hydroxyphenylglycyl and (2-amino-4-thiazolyl)(methoxyimino)acetyl.

34. The method of claim 24 wherein the prodrug is one in which Q is selected from the group consisting of: hydrogen, phenylacetyl, 2-thienylacetyl, α-hydroxyphenylacetyl, phenylglycyl, p-hydroxyphenylglycyl and (2-amino-4-thiazolyl)(methoxyimino)acetyl.

35. A method for the selective delivery of an antineoplastic agent to tumor cells comprising administering a pharmaceutically effective amount of at least one antibody-β-lactamase conjugate wherein said antibody is reactive with an antigen on the surface of said tumor cells; and administering a pharmaceutically effective amount of a compound of Count 1, which comprises a cephalosporin linked to said antineoplastic agent, whereby said antineoplastic agent is delivered to said tumor cells.

* * * * *